United States Patent
Lawrence et al.

(10) Patent No.: US 12,326,446 B2
(45) Date of Patent: Jun. 10, 2025

(54) SEQUENTIAL LATERAL FLOW DEVICE

(71) Applicant: Verax Biomedical Incorporated, Marlborough, MA (US)

(72) Inventors: Gregory M. Lawrence, Marlborough, MA (US); Adam P. Lousararian, Marlborough, MA (US); Yli Remo Vallejo, Marlborough, MA (US); Lisa Shinefeld, Marlborough, MA (US)

(73) Assignee: Verax Biomedical Incorporated, Marlborough, MA (US)

( * ) Notice: Subject to any disclaimer, the term of this patent is extended or adjusted under 35 U.S.C. 154(b) by 14 days.

(21) Appl. No.: 17/713,181

(22) Filed: Apr. 4, 2022

(65) Prior Publication Data
US 2022/0236265 A1  Jul. 28, 2022

Related U.S. Application Data

(62) Division of application No. 16/047,980, filed on Jul. 27, 2018, now Pat. No. 11,293,922.
(Continued)

(51) Int. Cl.
*G01N 33/543* (2006.01)
*B01L 3/00* (2006.01)
(Continued)

(52) U.S. Cl.
CPC ...... *G01N 33/54388* (2021.08); *B01L 3/5023* (2013.01); *B01L 3/502715* (2013.01);
(Continued)

(58) Field of Classification Search
CPC ......... G01N 33/54388; G01N 33/5304; G01N 33/566; G01N 33/56911; G01N 33/577;
(Continued)

(56) References Cited

U.S. PATENT DOCUMENTS 4,981,786 A * 1/1991 Dafforn ................ G01N 33/558
436/514
5,384,264 A * 1/1995 Chen ................ G01N 33/54366
436/805
(Continued)

FOREIGN PATENT DOCUMENTS

EP          1044372 A1    10/2000
JP       2003-517586 A     5/2003
(Continued)

OTHER PUBLICATIONS

Laverda, D. et al., "Improved Detection of Gram-Negative Platelet Isolates With Next-Generation Platelet PGD Test," the AABB Annual Meeting, Oct. 2015, [online], [retrieved on Sep. 27, 2022], Internet <URL:https://www.veraxbiomedical.com/wp-content/uploads/2020/02/Improved-Detection-AABB-Poster.1.pdf>.
(Continued)

*Primary Examiner* — Christopher L Chin
*Assistant Examiner* — Ellis Follett Lusi
(74) *Attorney, Agent, or Firm* — Morse, Barnes-Brown & Pendleton, P.C.; Lisa M. Warren, Esq.; Daniel L. Branson, Esq.

(57) ABSTRACT

The present disclosure provides methods and lateral flow devices for detecting a plurality of target analytes in a liquid sample. In some implementations, the disclosed lateral flow device comprises a housing unit, a capillary flow bed, a sample-receiving zone, a buffer-receiving zone, and a capture zone. The device is configured to control the flow of the sample and reagent buffer in a sequential manner with minimal mixing. In some implementations, the disclosed method is capable of detecting a plurality of target analytes in an assay by applying the binding agents and the signaling agents in separate or sequential steps.

18 Claims, 16 Drawing Sheets

Related U.S. Application Data

(60) Provisional application No. 62/537,701, filed on Jul. 27, 2017.

(51) Int. Cl.
 G01N 33/53 (2006.01)
 G01N 33/566 (2006.01)
 G01N 33/569 (2006.01)
 G01N 33/577 (2006.01)

(52) U.S. Cl.
 CPC ....... G01N 33/5304 (2013.01); G01N 33/566 (2013.01); G01N 33/56911 (2013.01); G01N 33/577 (2013.01); *B01L 2300/069* (2013.01); *B01L 2300/0825* (2013.01); *B01L 2400/0406* (2013.01)

(58) Field of Classification Search
 CPC ............ G01N 33/54386; G01N 33/558; B01L 3/5023; B01L 3/502715; B01L 2300/069; B01L 2300/0825; B01L 2400/0406
 USPC ............... 436/518, 169, 170, 514, 530, 810; 435/7.5, 7.92, 297.7, 287.9, 970, 805, 435/810; 422/400, 401, 420, 421, 425, 422/426, 430
 See application file for complete search history.

(56) References Cited

U.S. PATENT DOCUMENTS

| | | | |
|---|---|---|---|
| 5,773,234 A | 6/1998 | Pronovost | |
| 6,790,661 B1 | 9/2004 | Goodnow | |
| 7,371,582 B2 | 5/2008 | Nahm et al. | |
| 7,871,781 B2 * | 1/2011 | Rundstrom | G01N 33/54389 436/514 |
| 8,003,407 B2 | 8/2011 | Zhou | |
| 8,222,046 B2 * | 7/2012 | Xia | G01N 33/558 436/514 |
| 11,293,922 B2 | 4/2022 | Vallejo et al. | |
| 2008/0138842 A1 | 6/2008 | Boehringer et al. | |
| 2010/0221747 A1 | 9/2010 | Ito | |
| 2011/0129815 A1 | 6/2011 | Yamagaito et al. | |
| 2011/0136258 A1 | 6/2011 | Sambursky et al. | |
| 2013/0164193 A1 * | 6/2013 | Semenov | B01L 3/50273 422/507 |
| 2013/0217147 A1 | 8/2013 | Gibbons et al. | |
| 2013/0309656 A1 | 11/2013 | Davis | |
| 2015/0251177 A1 | 9/2015 | Kim | |
| 2016/0011185 A1 | 1/2016 | Lawrence | |
| 2019/0004042 A1 * | 1/2019 | Erickson | G01N 33/54388 |

FOREIGN PATENT DOCUMENTS

| | | | |
|---|---|---|---|
| JP | 2011-179865 A | 9/2011 | |
| WO | WO 90/008322 A1 | 7/1990 | |
| WO | WO-2000-025135 A1 | 5/2000 | |
| WO | WO 2001/006258 A1 | 1/2001 | |
| WO | WO-2002-044729 A1 | 6/2002 | |
| WO | WO 2007/069673 A1 | 6/2007 | |
| WO | WO-2008073222 A2 * | 6/2008 | ....... G01N 33/54306 |
| WO | WO-2014-055995 A1 | 4/2014 | |
| WO | WO-2019-023597 A1 | 1/2019 | |

OTHER PUBLICATIONS

Fridley, Gina E., Huy Le, and Paul Yager. "Highly sensitive immunoassay based on controlled rehydration of patterned reagents in a 2-dimensional paper network." Acatytical chemistry 86.13 (2014): 6447-6453.

Fu, Elain, ei al. "Controlled reagent transport in disposable 2D paper networks. Lab on a Chip," Royal Society of Chemistry, 10.7 (2010): 918-920.

Teiwes, Hanno. "A Paper-Based Lateral Flow Device for the Detection of I.alpha.IA Via Elisa". (2014).

International Search Report in International Application No. PCT/US18/44123 dated Nov. 28, 2018.

* cited by examiner

SEQUENTIAL LATERAL FLOW DEVICE

RELATED APPLICATIONS

This application is a divisional application of U.S. application Ser. No. 16/047,980, filed Jul. 27, 2018, (now U.S. Pat. No. 11,293,922), which claims the benefit of U.S. Provisional Application Ser. No. 62/537,701, filed Jul. 27, 2017, the entire teachings of which are incorporated herein by reference.

BACKGROUND

Lateral flow immunoassays (LFIs) are methods for the rapid detection of chemical and biochemical markers for toxicity and disease. LFIs can be classified into three types: (1) competitive assays such as those used to detect small molecule drugs of abuse and therapeutic drugs; (2) immunometric assays, also referred to as "sandwich" assays, for macromolecules such as proteins, glycoproteins, and lipopolysaccharides; and (3) serological assays, which detect antibodies to a specific antigen in a biological sample. This disclosure is focused on immunometric assays, for which the term "sandwich" assay will be used interchangeably for the sake of reference.

Sandwich LFIs (or immunometric LFIs) generally involve a bibulous flow path on which is immobilized a capture antibody and a mobilizable detector antibody that is attached to a signal-producing agent. The signal-producing agent is typically chosen from detectable colored and/or fluorescent particles, dyes, and/or enzymes. When the signal-producing agent is conjugated directly to the detector antibody, the term "direct assay" will be used.

Several patents and applications have described so-called sequential LFIs. A multi-port device is typically described in these applications as necessary to accommodate an extra reagent. In several patents and applications (e.g., U.S. Pat. No. 4,981,786, EP 1 044 372 B 1, US 2013/0164193), a primary use for the additional port is to separately and sequentially introduce a chromogenic and/or fluorogenic substrate reagent for an enzyme attached to a detector antibody. Other applications describe using a second port to enable the introduction of a wash buffer (e.g., U.S. Pat. No. 4,981,786). These assays, although sequential in the order of manipulations, are still direct assays in that the signal producing agent (e.g., enzyme) is directly conjugated to the detector antibody.

In examining the history of LFIs from its early concepts in the 1980s to the present day, the use of enzymes as signal-producing moieties on detector antibodies has diminished and has been supplanted by detector antibodies directly conjugated to signaling particles. Gold colloid and colored and/or fluorescent latex have found widespread and easier to use. The addition of a substrate is avoided when such signaling particles conjugated directly to detector antibodies are used.

In the course of developing and optimizing multi-analyte immunometric LFIs, we have found that immunometric assays that use detector antibodies directly conjugated to signaling particles suffer from decreasing sensitivity when more target analytes are present for detection via measurement on a single test strip. For example, if a sandwich LFI test strip were to detect three different target analytes, specific limits of detection (LoDs) for each analyte would be obtained. However, the LoDs would be degraded if an additional three target analytes were present in the sample mix (for a total of six target analytes). If another three target analytes were present in addition to the six target analytes for a total of nine target analytes for detection, the LoD for each target analyte would become even worse, to the point of eventual inutility.

These limitations are due, in part, to the surface area limit of the signaling particles and the limited conjugation capacity on the particle surface. These and other features of current methods and devices limit their applications. The present disclosure provides improved methods and devices that, among other things, address limitations of current approaches.

SUMMARY

In one aspect, the present disclosure provides improved methods and devices for detecting a plurality of target analytes, such as bacterial, viral, and/or fungal antigens, in a rapid, simple, sensitive, and multi-analyte manner. The disclosed methods and/or devices overcome some of the challenges and limitations of the conventional lateral flow devices and/or methods by allowing for running a binding assay using well-controlled sequential steps and innovative device features. Moreover, the methods and devices of this disclosure are particularly well-suited to detection of multiple target analytes, such as bacterial, fungal, and/or viral antigens, in a single assay using a plurality of binding agents, such as one or more than one types or idiotypes of antibodies (e.g., polyclonal antibodies) against numerous target-binding sites. In such settings where multiple antigens are being detected in complex samples using polyclonal antibodies as the binding agents, assay sensitivity is particularly crucial.

In one aspect, this disclosure provides a multi-analyte detection method, for example, an assay using a sandwich LFI test strip according to some implementations and/or a lateral flow device according to some implementations, that is able to detect as many as thirty, forty, or more possible target analytes in a liquid sample. For example, this disclosure describes a multi-analyte detection assay for detecting multiple species and strains of target analytes, such as bacterial antigens that potentially could infect platelet preparations intended for therapeutic and/or protective transfusion into patients. This disclosure also provides a rapid assay and/or test, such as an LFI (e.g., a sandwich LFI), which is considered an improvement as a safety measure over established culture-based tests as the disclosed assays or tests can be performed right before transfusion, while a culture test requires initiation of a test one to three days prior to transfusion.

A single LFI test strip used in conventional methods and/or devices is severely challenged in its ability to detect the variety of contaminating bacterial species and strains at the clinically relevant LoDs due to the limitations of particle conjugates, (or detector antibody-signaling particle conjugates), capacity for multi-analyte detection, especially for forty or more target analytes.

In one aspect, by separating the binding agent (e.g., a plurality of antibodies, such as one or more than one type of polyclonal antibodies) from the signaling agent (e.g., signaling particles) at the initiation of the LFI test procedure, and enabling the plurality of target analytes in the liquid sample to first form sandwich complexes at the capture zone before the release of the signaling agent, the constraint to sensitivity imposed by the limited number of binding agents on the surface of the detecting particle is significantly overcome. In this sequential manner, LoDs can be improved by two-fold to as much as two log-fold in a multiplexed assay, as compared to a similar multiplexed non-sequential direct assay.

In one approach, as long as the formation of the sandwich complexes (e.g., a complex between the binding agent, target analyte, and immobilized capture agent) at the capture zones occurs before the binding agent or analyte contacts the signaling agent. In some implementations, the liquid sample is optionally mixed with detector antibodies before being introduced into a lateral flow device. This procedure allows some of the detector antibodies to bind to some of the target analytes before entering the flow path. In addition, the number of required signaling particles can be reduced to only sufficient numbers to label the actual sandwich complexes. As the target analytes get captured by the capture agents immobilized on the flow path, the efficiency of labeling the target analyte with detector antibodies greatly increases as the reaction between the target analytes and the detector antibodies is no longer limited by diffusion. Excess of the detector antibodies may flow past the captured target analytes on the flow path for binding. The sensitivity of the assay is, therefore, driven by the number of effective binding events between the binding agent (e.g., detector antibodies) and the captured target analytes, rather than the number of binding agent-signaling agent conjugates or signaling agents bound to the target analytes and captured in the capture zone. Since the binding agents are a lot smaller in size than the binding agent-signaling agent conjugates or conjugates that are bound to analytes, higher local concentration of binding agents can be achieved in a given processed sample volume; in some cases this is in log-fold excess compared to the maximum number of signaling particles that the strip typically accommodates. Moreover, in a non-sequential assay, a large percentage of binding agent-signaling agent conjugates become captured at the capture zone without even binding to the target analytes, causing interference and lowering detection sensitivity.

In some implementations, by separating the binding agent (e.g., detector antibodies) from the signaling agent (e.g., signaling particles), the binding agent and the signaling agent in excess amount can be applied or flow sequentially across the capture zones in a controlled manner. In this way, a significant improvement in sensitivity can be achieved, allowing a greater multiplicity of target analytes to be detected, e.g., using a single LFI strip at the desired LoDs. A greater number of sandwich complexes can therefore be formed with the increased local concentrations of binding agents, which subsequently are "labeled" with signaling agents.

In addition, the disclosed methods and devices can detect a plurality of target analytes at clinically significant levels with improved sensitivity in a time-sensitive manner, for example, testing bacteria contamination in less than a few hours (e.g., less than four hours, less than three hours, less than two hours, and/or less than one hour). This facilitates, for example, the testing of blood and/or blood products prior to transfusion without the need of accelerated growth of bacteria and/or virus in nutrient media, which may take one to a few days.

In some aspects, this disclosure provides methods and devices for conducting an assay in a sequential multi-step manner, such as an immunoassay with sequential steps, for detection/determination of a plurality of target analytes in a liquid sample, such as blood or blood products. In exemplary implementations, the disclosed method detects multiple analytes using binding agents that are themselves complex, such as one or more than one type of polyclonal antibodies.

In one aspect, the disclosure provides a method for detecting a plurality of target analytes in a liquid sample using a lateral flow device. The method includes first contacting the liquid sample with a plurality of capture agents disposed on a solid support in the lateral flow device and a plurality of binding agents under conditions that permit formation of at least one sandwich complex comprising one or more of the plurality of binding agents, one or more of the target analytes, and one or more of the capture agents. Each of the binding agents is tagged with one member of a conjugate pair. In some implementations, the plurality of binding agents and the plurality of capture agents are antibodies. In some implementations, the plurality of binding agents and the plurality of capture agents are monoclonal antibodies, polyclonal antibodies, and/or mixtures thereof. In some implementations, the plurality of binding agents and the plurality of capture agents are polyclonal antibodies. In some implementations, the plurality of binding agents and/or the plurality of capture agents can bind to at least one antigen common to at least a subset of the target analytes. In some implementations, the plurality of target analytes may include multiple subsets or types of target analytes, such as bacteria (e.g., Gram-positive and/or Gram-negative bacteria), viruses, and/or fungi. Each type or subset of the target analytes may further include sub-types or different genera. Within each subset or type (or sub-types or genera) of target analytes, there may be a common antigen that the binding agents or capture agents can bind to. For example, the plurality of target analytes may include at least a subset of Gram-positive bacteria and/or a subset of Gram-negative bacteria and/or subtypes thereof. Each of the binding agents and/or capture agents can bind to an antigen common to at least a subset of Gram-positive bacteria or subtypes thereof and/or bind to an antigen common to at least a subset of Gram-negative bacteria or subtypes thereof. Due to the antigenic diversity among species, multiple types of binding agents may be used. Following the formation of the sandwich complex, a signaling agent (e.g., non-enzymatic signaling agent) is introduced to the device and brought into contact with the sandwich complex under conditions that permit the signaling agent to bind to a binding agent of the sandwich complex to form a detection complex (e.g., through the interactions of the conjugate pair). Formation of the detection complex indicates the presence of one or more of the plurality of the target analytes as the signaling agent produces a detectable signal where the detection complex is formed in the device. The lateral flow device is adapted to inhibit the signaling agent from contacting the plurality of binding agents prior to the formation of the sandwich complex. A signal generated by the formation of the detection complex is detected to determine the presence of the target analytes. In one aspect, the signaling agent is a non-enzymatic agent, which allows direct detection of the signal without resorting to amplification techniques, such as PCR amplification or amplification based on products of catalytic enzymatic reactions. In this way, the disclosed methods or devices include a simplified detection step, reducing the cost for operating and/or manufacturing. While prior LFIs may have incorporated some degree of sequential treatment of the reagents, this sequential treatment was forced by the use of enzymatic assays to generate signals in situ (e.g., an enzymatic signaling agent). In addition, enzymatic assays are affected by factors such as temperature and enzyme/substrate concentrations and may be interfered by the presence of any inhibitors or activators, which are not directly related to the determination of the target analytes. Therefore, directly detecting the sandwich complexes using a signaling agent such as a signaling particle may circumvent these potential issues and reduce the possibility of false-positive results or various potential interfering factors in the detection step.

In some implementations, the lateral flow device includes a substantially impermeable backing disposed between a sample-receiving pad in the sample-receiving zone for introducing the liquid sample into the lateral flow device and a capillary flow bed in the solid support that facilitates a flow of the liquid sample. As such, backflow of the liquid sample in the proximal direction of the lateral flow device is reduced or minimized. In some implementations, the lateral flow device comprises a housing unit, wherein the upper inner surface of the housing unit comprises a series of ribs to contain liquid in excess of the capacity of the sample-receiving pad, thereby inhibiting the excess fluid from overflowing the sample-receiving pad.

In some implementations, the sandwich complex can be formed in one step by flowing a mixture of the liquid sample and the plurality of binding agents through the capture zone to come into contact with the capture agents. Under suitable conditions, sandwich complexes may be formed between the one or more of the plurality of binding agents, one or more of the target analytes, and one or more of the capture agents. According to some implementations, a sequential flow of sample and reagents through the capture zones to the distal end of the assay strip may be achieved by first flowing the liquid sample and a plurality of binding agents (e.g., detector antibodies), which are not conjugated to signaling agents, followed by a separate release and flow of signaling agents (e.g., signaling particles) that can attach to a binding agent of the sandwich complex in a subsequent step. By doing so, there is little or no mixing of the two sequential fluid flows to help achieve an improved sensitivity.

In some implementations, formation of the sandwich complex may be achieved in two steps. The first step includes contacting the liquid sample with a plurality of binding agents to form a first complex between at least some of the target analytes and at least some of the binding agents. The second step includes contacting the first complex with a plurality of the capture agents immobilized on a solid support under conditions that permit the plurality of capture agents to bind to the first complex to form the sandwich complex. In some implementations, a first complex may be formed by simply mixing the liquid sample and a solution containing a plurality of binding agents in a test tube by a person; and/or by adding the liquid sample into a device (such as any of the devices described herein), such as a lateral flow device and/or a test strip, pre-loaded with the plurality of binding agents in which the liquid sample will mix with the plurality of binding agents inside the device.

In some implementations, mixing the liquid sample with a plurality of binding agents can be carried out in a buffer solution at room temperature and/or with slight heating and/or agitation. Sufficient time should be given so that the binding between the target analytes and the binding agents can be as complete as possible. In some implementations, the plurality of binding agents may be selected so as to detect three or more target analytes (e.g., five, ten, twenty, thirty, and forty or more target analytes). The disclosed method is able to detect a greater number of target analytes without compromising the sensitivity of the test by using a sequential flow mechanism.

In some implementations, following the formation of the first complex, sandwich complexes can be formed by flowing a buffer solution containing the first complex over the immobilized capture agents on the solid support. In one implementation, the solid support is a lateral flow bed in a lateral flow device (such as a device described herein). Excess amount of the first complexes that do not form the sandwich complex with the capture agents may be removed, e.g., by washing the solid support with a buffer solution. Alternatively, the unbound first complexes may flow past where the immobilized capture agents are toward a reservoir in a lateral flow device, such as a device described herein. Suitable conditions may be applied to facilitate the formation of the sandwich complex, such as using a buffer solution, slightly heating the solid support, or adjusting the proper pH level.

Formation of the sandwich complex may also be achieved by contacting the liquid sample with the plurality of immobilized capture agents first to form a complex comprising at least some of the target analytes and at least some of the capture agents, then followed by contacting a plurality of binding agents with the complex. In some implementations, all of the liquid sample that contains the plurality of target analytes may be brought into contact with the capture agents. As such, the close proximity of the target analytes and the capture agents effectively increases the local concentration of both for interaction.

Each of the plurality of binding agents (e.g., detector antibodies) may be tagged with a small molecule (e.g., a small molecule of less than about 1000 MW) that is one member of a conjugate pair, and the signaling agent (e.g., signaling particle) may be tagged with the other member of the conjugate pair. For example, biotin may be covalently attached to the binding agent (e.g., detector antibody), and an avidin analogue (e.g., streptavidin, neutravidin, anti-biotin antibody, etc.) may be coated on the surface of the signaling particle, or vice versa. In this manner, the signaling particles can attach to the detector antibodies, but only after the sandwich complexes have been formed, e.g., at the capture zones of a test strip. In some implementations, the plurality of binding agents, such as detector antibodies labeled with biotin, are about a tenth of the size of about a 100 nm particle-detector antibody conjugate.

The binding agents may include one or more than one type of binding agent (e.g., two, three, four, five, 10, 15, 20, 30, 40 or more different types of binding agents) depending on the number and types of target analytes. In some implementations, the binding agents include antibodies (e.g., monoclonal antibodies and/or polyclonal antibodies), such as antibodies that specifically bind to a common antigen of at least a subset of target analytes (e.g., a plurality of Gram-negative and/or Gram-positive bacteria in the liquid sample). The target analytes may include multiple types or subset of analytes and within each types or subset, there may be multiple sub-types. Each of the types or subsets or subtypes thereof may have an antigen common to the analytes within said type or subset or subtypes thereof to which the binding agent can specifically bind. The binding agents may be polyclonal antibodies, such as one or more than one type of polyclonal antibodies. In some implementations, the binding agents can specifically binds to at least one antigen common to at least a subset of Gram-positive and/or Gram-negative bacteria or a subtype within the foregoing. In some implementations, the binding agents are selected from one or more than one type of polyclonal antibodies and monoclonal antibodies. Each of the binding agents may be associated with a first member of a conjugate pair, such as a biotin and biotin-binding protein pair. The biotin-binding protein may be selected from the group consisting of avidin, neutravidin, anti-biotin antibody, streptavidin, and other biotin-binding proteins.

In some implementations, the capture agents include one or more than one type of capture agents (such as one or more than one type of polyclonal antibodies). For example, the capture agents may include two, three, four, five, 10, 15, 20, 30, 40, or more types of capture agents depending on the number and types of target analytes. In some implementations, the capture agents is adapted to specifically bind to at least one antigen common to at least the subset of target analytes or subtypes thereof in the liquid sample. In some implementations, the plurality of capture agents are selected from one or more than one types of polyclonal antibodies and/or monoclonal antibodies. In some implementations, the plurality of capture agents include one or more than one capture grouping on the solid support, the groupings spatially separated from each other and each grouping including at least a capture agent that specifically binds to a different common antigen of at least a subset of target analytes (e.g., an antibody that specifically binds to a different target analyte). In some implementations, at least some of the binding agents are different types of antibodies from at least some of the capture agents. In some implementations, at least some of the binding agents are the same type of antibodies as at least some of the capture agents.

The disclosed method also includes forming a detection complex for providing a readable signal to indicate the presence of the plurality of target analytes in the liquid sample. Formation of the detection complex is achieved by contacting the sandwich complex with a signaling agent under conditions that permit the signaling agent to bind to a binding agent of the sandwich complex, which indicates the presence of one or more of the plurality of the target analytes. The signal generated by the signaling agents upon forming the detection complex is used to determine the presence of the plurality of target analytes. The signaling agent is tagged with a second member of the conjugate pair, such as a biotin and biotin-binding protein pair. In some implementations, the conjugate pair comprises biotin and a biotin-binding protein and either the binding agent or the signaling agent is labeled with biotin. In some implementations, the biotin-binding protein is selected from the group consisting of avidin, neutravidin, anti-biotin antibody, streptavidin, and other biotin-binding proteins. In some implementations, each of the plurality of binding agents is associated with avidin and/or streptavidin. In some implementations, the signaling agent is selected from the group consisting of metallic particles, fluorescent dyes, and latex particles. The binding of the signaling agent to a binding agent of the sandwich complex indicates the presence of the plurality of target analytes in the liquid sample.

By introducing the signaling agent after the formation of the sandwich complex, the sensitivity of the method is increased as an increasing number of the sandwich complexes have been formed prior to signal detection, as a result of the increased binding events between the binding agents and the target analytes. The limitations imposed by the large size and limited conjugation density of the binding agent-signaling agent conjugates as used in the conventional methods have been obviated, thereby, permitting more of the target analytes to bind with the binding agents, to potentially generate more of the sandwich complexes for detection. The signal generated by the formation of the detection complexes is detected to determine the presence of the plurality of target analytes. Depending on the nature of the signaling agent employed in the method, the signaling agent is capable of producing a detectable signal such as a visual signal, a chemically detectable signal, an electrical signal, and/or a signal detectable by an instrument and/or by a person to report the formation of the third complex. In some implementations, the detection is by measuring an optical signal either by naked eye and/or by an optical instrument. In some implementations, the detection is through measuring an electrical signal using electrodes in a buffer solution in the presence of the third complex. In some implementations, the steps of the methods described herein are automated, for example, when a device (e.g., a device described herein) is employed, each step can be automated and a person will apply the liquid sample to the device via an inlet. In these situations, a buffer solution may also be applied to the device simultaneously and/or sequentially via a second inlet to the device for mobilizing the binding agents and/or the signaling agents.

In some implementations, the methods described herein can be carried out with a test strip on which the plurality of capture agents are immobilized, such as a test strip similar to the lateral flow bed/path in a lateral flow device described herein. The test strip may comprise a bibulous material in which the liquid sample and/or buffer will flow along the strip under capillary force. When a plurality of target analytes are present in the liquid sample above a certain detection threshold (e.g., a clinically relevant threshold), a detection complex may be formed and provide a detectable signal indicating a positive result. In situations where there is no target analyte present in the liquid sample or the concentrations of the plurality of target analytes are below a certain detectable threshold, no detectable signal will be collected and/or observed, indicating a negative result.

In some implementations, the method may comprise obtaining a liquid sample, such as a blood and/or platelet sample, e.g., a sample from a previously stored bag of blood and/or platelets potentially suitable for transfusion. In some implementations, the sample may be further processed before being applied to a method and/or introduced into a device of the present disclosure. A device, as described herein, is used to identify the presence of bacterial, viral and/or fungal contamination in a liquid sample. In some implementations, the detection and/or method can be carried out prior to use of the blood and/or blood product in transfusion, thereby reducing the risk of transfusing a patient with contaminated blood product. In some implementations, the sample is pre-treated using a base digestion followed by neutralization. In some implementations, the pre-treated liquid sample is optionally mixed with a plurality of binding agent prior to the assay or being introduced to the device. In some implementations, the plurality of target analytes includes a bacterial antigen, a viral antigen, and/or a fungal antigen.

In some aspects, this disclosure provides a sequential lateral flow device, for example, a device for performing the methods described herein. The sequential lateral flow device may be used to implement any of the methods described herein for detecting a plurality of target analytes, including those described in the preceding paragraphs.

In some implementations, the sequential lateral flow device includes a housing unit comprising an inner surface that defines a cavity in the housing unit. In some implementations, the sequential lateral flow device includes a capillary flow bed residing in the cavity, wherein the capillary flow bed is configured to transport the sample from a proximal region of the capillary flow bed to a distal region of the capillary flow bed. In some implementations, the sequential lateral flow device includes a buffer-receiving zone comprising a buffer-receiving pad ($P_B$) and a conjugate pad ($P_C$). The conjugate pad includes a signaling agent for providing a detectable signal. In some implementations, the sequential lateral flow device includes a capture zone (C) comprising a plurality of immobilized capture agents. In some implementations, the sequential lateral flow device includes a sample-receiving zone disposed between the buffer-receiving zone and the capture zone, the sample-receiving zone comprising a sample-receiving pad ($P_S$), a transfer pad ($P_T$), and a substantially impermeable backing disposed between the sample-receiving zone and the capillary flow bed and extending at least partially underneath the sample-receiving pad and the transfer pad. In some implementations, the transfer pad includes a plurality of binding agents that specifically bind to a plurality of target analytes. In some implementations, the sequential lateral flow device includes a reservoir pad (R) disposed in the distal region of the capillary flow bed. In some implementations, the sequential lateral flow device includes a first inlet ($I_1$) in said housing for introducing the sample into the sample-receiving pad. In some implementations, the impermeable backing inhibits contact between the sample and the capillary flow bed in the sample-receiving zone, thereby reducing backflow of the liquid sample in a proximal direction. In some implementations, the sequential lateral flow device includes a second inlet ($I_2$) in said housing for introducing a buffer into the buffer-receiving pad. In some implementations, the buffer mobilizes the signaling agent to obtain a mobilized signaling agent. In some implementations, the sequential lateral flow device includes a reading window defined in the housing unit over the capture zone for observing a detectable signal produced by an interaction of the plurality of binding agents and the signaling agent in the presence of the plurality of target analytes. In some implementations, the reservoir pad is adapted to draw the liquid sample and the mobilized signaling agent in the distal flow direction. In some implementations, the device is configured such that the sample flows along the capillary flow bed into the capture zone before the mobilized signaling agent flows into the capture zone.

In some implementations, the sample-receiving zone, the buffer-receiving zone, the capture zone, and the reservoir pad are arranged from the proximal region to the distal region on the capillary flow bed as shown in FIG. 15.

In some implementations, the inner surface of the housing unit includes a series of ribs adapted to retain excess fluid, thereby inhibiting the excess fluid from overflowing the sample-receiving pad, the buffer-receiving pad, and/or the capillary flow bed. For example, in such implementations, if a user of the device adds an excessive amount of the buffer reagent at the second port that exceeds the capacity of the buffer-receiving pad, the ribs in the housing are designed to contain the excess liquid. The same may also be true of the sample-receiving pad and transfer pad.

In some implementations, the series of ribs are disposed over the sample-receiving pad on the upper inner surface of the housing unit.

In some implementations, the series of ribs are disposed over the buffer-receiving pad on the upper inner surface of the housing unit.

In some implementations, the inner surface of the housing unit includes at least one pinch unit pressing the buffer-receiving pad into the conjugate pad to create a flow path for the buffer to flow from the buffer-receiving pad to the conjugate-pad.

In some implementations, the inner surface of the housing unit includes at least one pinch unit pressing the sample-receiving pad into the transfer pad to create a flow path for the sample to flow from the sample-receiving pad to the transfer-pad.

In some implementations, the inner surface of the housing unit includes at least one pinch unit pressing the transfer pad into the flow path bed to create a flow path for the sample from the transfer-pad to the capillary flow bed.

In some implementations, the capillary flow bed is slightly bent to promote capillary action and minimize flooding.

In some implementations, the plurality of capture agents in the capture zone comprise one or more than one type of capture agents each adapted to specifically bind to a common antigen of at least a subset of target analytes in the liquid sample.

In some implementations, the plurality of capture agents bind a Gram-positive and/or Gram-negative bacterial antigen.

In some implementations, a plurality of the capture agents includes antibodies (e.g., polyclonal antibodies, such as multivalent polyclonal antibodies).

In some implementations, the plurality of capture agents are selected from one or more than one types of a polyclonal antibody and a monoclonal antibody.

In some implementations, the plurality of capture agents include one or more capture agent groupings on the capillary flow bed, the groupings spatially separated from each other, each grouping comprising an antibody that specifically binds to a different common antigen of at least a subset of target analytes.

In some implementations, the plurality of binding agents can bind a Gram-positive and/or Gram-negative bacterial antigen.

In some implementations, the plurality of binding agents comprise antibodies. In some implementations, the antibodies are selected from one or more of a polyclonal antibody and/or a monoclonal antibody.

In some implementations, each of the plurality of binding agents is associated with a first member of a conjugate pair, and the signaling agent is labeled with a second member of the conjugate pair.

In some implementations, the conjugate pair is biotin and a biotin-binding protein, and either each of the plurality of binding agents or each of the plurality of signaling agents is labeled with biotin.

In some implementations, the signaling agent is selected from the group consisting of metallic particles, fluorescent dyes, and latex particles.

In some implementations, the biotin-binding protein is selected from the group consisting of avidin, NeutrAvidin, anti-biotin antibody, streptavidin, and other biotin-binding proteins.

In some implementations, the capillary flow bed includes nitrocellulose.

In some implementations, the sample-receiving pad, the buffer-receiving pad, the reservoir pad, and the conjugate pad each comprise a bibulous material.

In some implementations, the bibulous material is selected from the group consisting of porous paper, polypropylene, polyester, polyethylene, glass fibers, cellulose blends, and a combination thereof.

In some implementations, the sample is pre-treated using a base digestion followed by neutralization.

In some implementations, the plurality of target analytes include a bacterial antigen, a viral antigen, and/or a fungal antigen.

In some aspects, the present disclosure provides a method for detecting a plurality of target analytes in a liquid sample using any lateral flow device described herein.

In some implementations, the detecting a plurality of target analytes in a liquid sample using any lateral flow device described herein includes the following steps:

(a) the liquid sample may be introduced into the lateral flow device through the first inlet. The liquid sample flows from the sample-receiving pad to the transfer pad, and the liquid sample is prevented from contacting the capillary flow bed by the backing prior to contacting a distal portion of the transfer pad.

(b) the plurality of target analytes, if present in the sample, form a first complex with a plurality of binding agents in the transfer pad. The first complex is drawn toward the capture zone through the capillary flow bed by capillary force produced by the reservoir pad disposed in the distal region of the capillary flow bed.

(c) a buffer may be introduced into the second inlet of the lateral flow device to mobilize the signaling agent after introducing the liquid sample, such that the mobilized signaling agent flows into the capture zone after the sample flows past the viewing window over the capture zone.

(d) a detectable signal produced in the capture zone may be read through the reading window.

In some implementations, the sample may be added into the sample-receiving pad using a dropper with a fixed, predetermined volume/capacity calibrated to the capacity of the sample-receiving pad. In some implementations, a fixed amount of the liquid sample, for example 45 µL to 50 µL of liquid sample, may be added, using the dropper, into the sample-receiving pad, which is greater than the saturation capacity of the sample-receiving pad.

The disclosure contemplates combinations of any of the foregoing aspects, embodiments, and implementations with each other, as well as with any one or more of the features set forth herein.

BRIEF DESCRIPTION OF DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION

Figure 1:
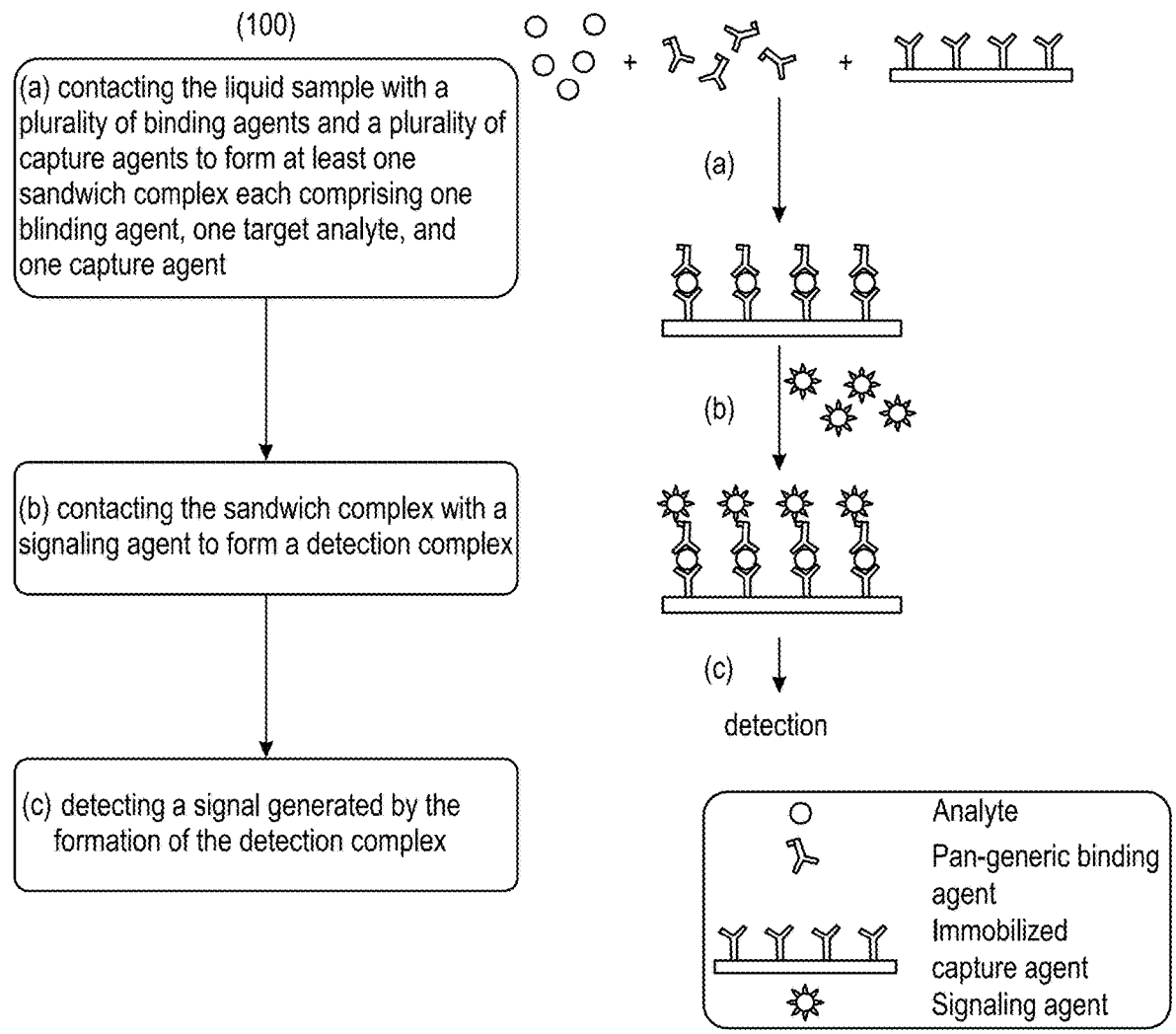
FIG. 1 shows a flow chart of the sequence of steps in a method for detecting a plurality of target analytes in a liquid sample according to some implementations.

Unless otherwise defined herein, scientific and technical terms used in this application shall have the meaning commonly understood by those skilled in the art. The techniques and procedures described or referenced herein are well understood and commonly employed using conventional methodologies that are well known and commonly used in the art.

All publications, patents and published patent applications referred to in this application are hereby specifically incorporated by reference herein.

Each implementation of the disclosure described herein may be taken alone and/or in combination with one or more other implementations of the disclosure.

Unless specified otherwise, the following definitions are provided for specific terms, which are used in the above written description.

Throughout this disclosure, the word "comprise" and/or variations such as "comprises" and "comprising" will be understood to imply the inclusion of a stated integer (or components and/or steps) or group of integers (or components and/or steps), but not the exclusion of any other integer (or components and/or steps) or group of integers (and/or components).

The singular forms "a," "an," and "the" include the plurals unless the context clearly dictates otherwise. "A" or "an" also means "one or more" or "at least one."

Transitional terms such as "including," "having," "containing," "involving," "composed of," and the like are to be understood to be open-ended and are used to mean "including but not limited to." "Including" and "including but not limited to" are used interchangeably.

As used herein, a binding agent is an agent capable of binding more than one genus of bacteria, viruses, and/or fungi. Binding agents are capable of binding to a common antigen of more than one genus of bacteria, viruses, and/or fungi, when used in the methods and devices of the present disclosure, for example, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, or twenty or more genera of bacteria, viruses, and/or fungi. In some implementations, the binding agent is an antibody. In some implementations, a plurality of binding agents are used in the methods and devices described herein. The plurality of binding agents can be one or more than one type of binding agents, such as one or more than one type of antibodies, each adapted to specifically bind to a common antigen of at least a subset of target analytes and the target analytes may include multiple subsets or types of analytes, each subset or type having a common antigen within the subsets. In some implementations, a binding agent specifically binds a common antigen in more than one genus of bacteria, viruses, and/or fungi. By way of non-limiting example, an antibody that specifically binds lipopolysaccharide on two or more genera of Gram-negative bacteria is a binding agent. Likewise, an antibody that specifically binds lipoteichoic acid (LTA) on two or more genera of Gram-positive bacteria is a binding agent. Such binding agents can be polyclonal and/or monoclonal antibodies. In some implementations, a binding agent comprises antibodies with different specificities in a mixture, such that the mixture binds more than one genus of bacteria, viruses, and/or fungi. Other non-antibody molecules may serve as binding agents if they have the capability of binding to components of bacteria, viruses, and/or fungi (e.g., antibiotics such as polymyxin bind to lipopolysaccharides of multiple genera of Gram-negative bacteria, and vancomycin can bind to components of the cell wall of Gram-positive bacteria). These molecules, with a suitable linker, could be used as binding agents.

As used herein, "antigen" (for example, a Gram-negative bacterial antigen and/or a Gram-positive bacterial antigen) is used to mean any molecule, in any structural conformation that may be specifically bound by a binding agent. The site on the antigen that is bound by a binding agent is called a "binding site." An antigen may be, without limitation, a protein, a glycoprotein, a carbohydrate, and/or a lipid.

As used herein, "analyte" or "analytes" refers to species, substances, and/or compounds to be detected and/or quantitatively analyzed in a sample. Analytes include but are not limited to toxins, proteins, peptides, viruses, bacteria and/or bacteria antigens, nucleic acids, carbohydrates, fungi, steroids, hormones, polysaccharides, carbohydrates, pollutants, metabolites, antibodies, and/or any detectable substances from human and/or non-human sources, such as blood, tissue, water, soil, sewage, beverages. In some implementations of this disclosure, an analyte binds to a binding agent and forms a first complex, and then the first complex binds to the immobilized capture agents on the capillary flow bed in the capture zone and forms a sandwich complex between the first complex and the capture agent. In certain such implementations, the sandwich complex further binds to a signaling agent to form a detection complex. The formation of each complex is discrete and sequential.

As used herein, "a conjugation pair" or "a conjugate pair" refers to two different molecules/members in which the first and second molecule/member bind to each other through a covalent bond, affinity, and/or physical means. The binding or interaction between the members of the conjugation pair is specific and unique such that the members are capable of distinguishing their binding partners from various interactions and/or affinities from other components of an assay and/or surrounding substances. In some implementations, a conjugation pair can be a receptor and a ligand, such as an antibody and an antigen. In other implementations, a conjugation pair includes, but is not limited to, biotin and avidin, carbohydrates and lectins, complementary nucleotide sequences, complementary peptide sequences, effector and receptor molecules, enzyme cofactors and enzymes, enzyme inhibitors and enzymes, a peptide sequence and an antibody specific for the sequence or the entire protein, polymeric acids and bases, dyes and protein binders, peptides and specific protein binders (e.g., ribonuclease, S-peptide and ribonuclease S-protein), metals and their chelators, and the like. Furthermore, specific binding pairs can include members that are analogs and/or derivatives of the original specific binding member, for example, a specific binding member made by chemical modification, recombinant techniques, and/or molecular engineering that still maintains similar binding properties to the other binding member. In some implementations, a first member of a conjugation pair is biotin and a second member of a conjugation pair is selected from avidin, NeutrAvidin, streptavidin, and/or any anti-biotin antibody.

This disclosure provides methods, sequential lateral flow devices, and kits for detecting one or more target analytes in a liquid sample. This disclosure also provides methods of using the disclosed devices and/or kits. It is to be understood that this disclosure is not limited to the implementations set forth herein. It is also to be understood that the implementations of this disclosure are intended for descriptive purposes and should not be deemed as limiting.

In some implementations, this disclosure provides methods, devices, and kits with broader reactivity and higher sensitivity than existing methods, devices, and kits. In some implementations, the methods, devices, and kits are capable of detecting a broader range of target analytes, such as a broader range of bacterial genera, species, and/or strains of bacteria than existing methods and devices. For example, the methods, devices, and/or kits may be capable of detecting at least 20, 40, 60, 80, 100, 150, 200, 250, 300, 350, 400, 450, or 500 different bacteria, virus, or fungi. In some implementations, the disclosure provides methods, devices, and/or kits comprising a plurality of antibodies capable of detecting greater than $1\times10^7$, $1\times10^6$, $1\times10^5$, $1\times10^4$, $1\times10^3$, or $1\times10^2$ colony forming units (CFU) per mL of bacteria and/or an equivalent concentration of antigens derived from that level of bacteria, each of which antibodies can bind to a common antigen of at least a subset of the target analytes.

Detailed descriptions of certain implementations suitable for the devices, kits, and methods of this disclosure are discussed as follows, but not limited to:

FIG. 1 shows an illustrative method (100) for detecting a plurality of target analytes in a liquid sample, according to some implementations. In step (a), the liquid sample is brought into contact with a plurality of binding agents and a plurality of capture agents on a solid support in a lateral flow device under conditions that permit formation of at least one sandwich complex. The sandwich complex is formed between one or more of the plurality of the binding agents, one or more of the target analytes, and on one more of the capture agents. The sandwich complex may be formed in a step-wise manner, such as the target analyte may bind to the binding agent first before binding with the capture agent or the target analyte may bind to the capture agent first before binding with the binding agent. In some events, the target analyte, binding agent, and the capture agent may come together to form the sandwich complex in one-step. In some implementations, the plurality of binding agents and the plurality of capture agents are antibodies. In some implementations, the plurality of binding agents and the plurality of capture agents are monoclonal antibodies, polyclonal antibodies, and/or mixtures thereof. In some implementations, the plurality of binding agents and the plurality of capture agents are polyclonal antibodies. The sandwich complex includes at least one target analyte (in the middle), one or more of the capture agents (at the bottom, immobilized to a solid support), and one or more of the plurality of binding agents (on the top). Unbound reagents, target analytes, and/or binding agents may be optionally washed away and/or removed prior to the next step, for example, by washing the solid support with a buffer solution and/or spinning dry the solid support. When the method is carried out on a device, such as a lateral flow device described herein, unbound reagents may be carried away from the capture agents via capillary force.

In some implementations, the plurality of binding agents and/or the plurality of capture agents are antibodies (e.g., polyclonal antibodies or monoclonal antibodies). In some implementations, such antibodies can specifically bind a common antigen of at least a subset of Gram-positive and/or Gram-negative bacteria and/or at least a subtype thereof. In certain implementations, the plurality of binding agents or the plurality of capture agents can be a polyclonal antibody (e.g., a multivalent polyclonal antibody), a monoclonal antibody, and/or a mixture of the foregoing. In some implementations, each of the plurality of binding agents is tagged with one member of a conjugate pair, such as a conjugate pair of biotin and a biotin-binding protein (e.g., avidin, neutravidin, anti-biotin antibody, streptavidin, and/or other biotin-binding proteins). Unlike the binding agent-signaling particle conjugates used in conventional methods, the binding agent in the present method is tagged with a first member of a conjugate pair, e.g., a small molecule such as biotin, according to some implementations. As such, the size of the binding agent is much smaller than the binding agent-signaling particle conjugates. Within the same reactive space, local concentrations of binding agents can be greatly increased thereby yielding increased binding events to generate higher numbers of the first complex for the next step and eventually for detection. In some implementations, the binding agent is labeled with biotin. In some implementations, the binding agent is labeled with a biotin-binding protein. Suitable conditions that may facilitate the formation of the sandwich complex include carrying out the reaction in a buffer solution (e.g., a phosphate buffer) at room temperature, optionally with agitation and/or slight heating. Optionally, unbound target analytes or binding agents may be removed prior to the next step.

In some implementations, the plurality of capture agents may be one or more types of capture agents each adapted to specifically bind to a common antigen of at least a subset of target analytes in the liquid sample. For example, in some implementations, the capture agents can specifically bind a common antigen of at least a subset of Gram-positive and/or Gram-negative bacteria and/or at least a subtype thereof. In some implementations, the capture agents are antibodies, such as polyclonal antibodies (e.g., a multivalent polyclonal antibody), monoclonal antibodies, and/or a mixture of the foregoing. In some implementations, at least some of the capture agents are the same type as at least some of the binding agents. In some implementations, at least some of the capture agents are different types from at least some of the binding agents. In some implementations, the plurality of capture agents are immobilized in groups on a solid support (e.g., a test strip and/or a capillary flow bed of a device described herein) covalently through a chemical bond and/or through physical absorption. The groupings may be spatially separated from each other with each grouping including an antibody that specifically binds to a different target analyte.

The process continues at step (b), a signaling agent (e.g., non-enzymatic) is brought in contact with the sandwich complex under conditions that permit the signaling agent to bind to a binding agent of the sandwich complex to form a detection complex. The signaling agent is tagged with a second member of the conjugate pair, and binding of the signaling agent to the binding agent of the sandwich complex indicates the presence of one or more of the plurality of the target analytes in the liquid sample. As such, the detection complex will also be immobilized on the solid support where the capture agents are. The lateral flow device is adapted to inhibit the signaling agent from contacting the plurality of binding agents prior to formation of the sandwich complex. In some implementations, the lateral flow device includes a substantially impermeable backing disposed between a sample-receiving pad in a sample-receiving zone for introducing the liquid sample into the lateral flow device and a capillary flow bed in the solid support that facilitates a flow of the liquid sample, thereby reducing backflow of the liquid sample in a proximal direction of the lateral flow device. In some implementations, the liquid sample may be added into the sample-receiving pad using a dropper with fixed volume/capacity calibrated to the saturation capacity of the sample-receiving pad. In some implementations, the amount of liquid sample added by using the dropper is less than the full saturation capacity of the sample-receiving pad so that the sample-receiving pad may be unsaturated.

The signaling agent provides a detectable signal where the detection complex is formed on the solid support to indicate the presence of the one or more of the plurality of target analytes in a liquid sample. In some implementations, the signaling agent is a colored particle, a latex particle, a metallic particle (e.g., gold, silver, platinum nanoparticles), a fluorescent particle, or a magnetic particle. In some implementations, the signaling agent is a colored dye and/or a fluorescence dye. In some implementations, the signaling agent is a catalytic enzyme. In some implementations, the signaling agent is a particle, such as a gold nanoparticle (e.g., a 40 nm, 60 nm, or 80 nm gold nanoparticle). In certain such implementations, the gold nanoparticle is tagged with a second member of the conjugate pair, and binding of the signaling agent to the binding agent of the sandwich complex (e.g., via the conjugate pair) indicates the presence of the one or more of the plurality of target analytes in the liquid sample. In certain such implementations, the signaling agent is a gold nanoparticle tagged with a biotin-binding molecule, such as avidin and/or streptavidin. Excess signaling agents may be washed away and/or removed before signal detection to minimize interference.

The process continues in step (c) where a signal generated by the formation of the detection complex is detected to determine the presence of the one or more of the plurality of target analytes in the liquid sample. The signal may be detected using appropriate means, such as visual, electrical, and/or optical detection. If the one or more target analytes are present in the liquid, and the detection complex is formed in a sufficient amount, a signal will be detected, e.g., on the solid support where the capture agent is immobilized, producing a positive result. However, in the absence of the one or more target analytes or if the one or more target analytes are not present in clinically relevant levels, neither the first, sandwich, nor detection complex will be formed in sufficient amounts and therefore, no detectable signal will be found, thereby producing a negative result.

Figure 2:
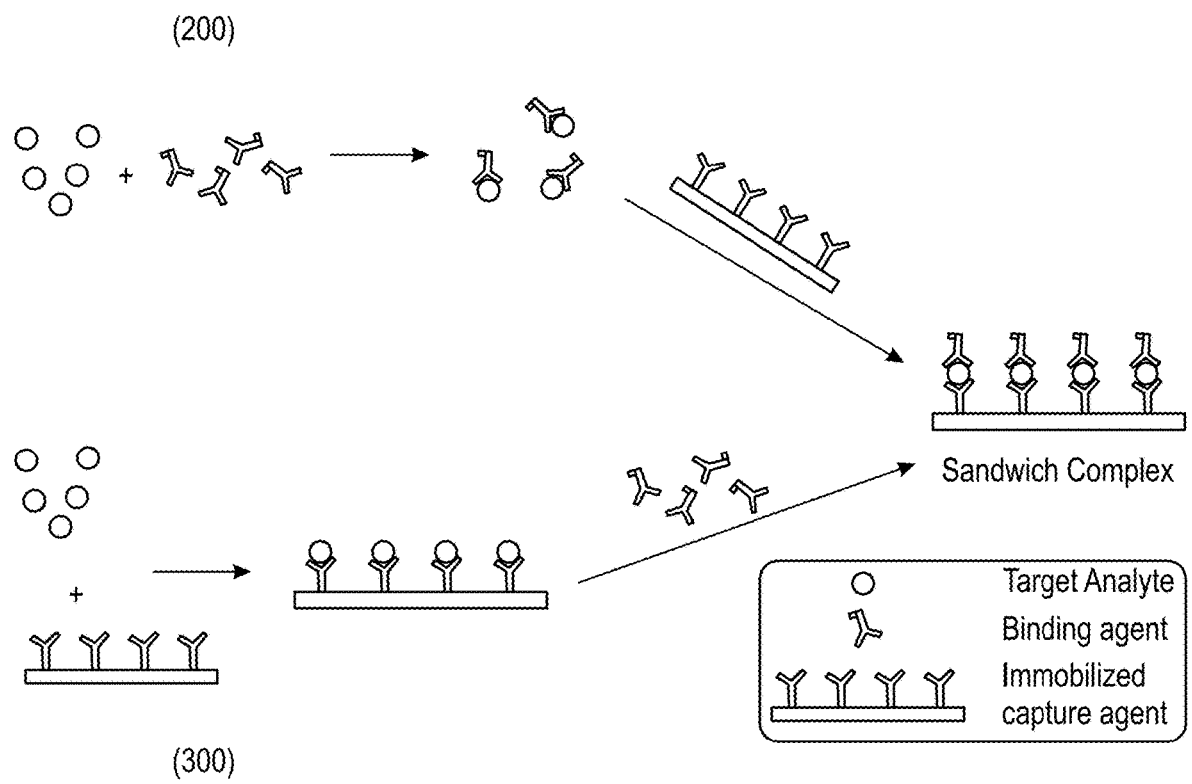
FIG. 2 shows formation of sandwich complexes via two-step routes according to some implementations.

FIG. 2 shows two routes to form sandwich complexes, each route having two steps according to some implementations. In the first route (200), the liquid sample is brought into contact with the plurality of binding agents under conditions that permit formation of a first complex between at least some of the target analytes and at least some of the binding agents. Subsequently, the first complex is brought to contact with the plurality of capture agents to form the sandwich complex, such that the liquid sample contacts the plurality of capture agents after formation of the first complex. In operation, the liquid sample can be simply mixed with the plurality of binding agents in a test tube prior to flowing through a device described herein. The solution containing the first complex can also be brought into contact the solid support on which the capture agent is immobilized by dipping the solid support in the solution for a sufficient amount of time. Alternatively, the liquid sample can flow through a device, such as a lateral flow device (e.g., a device described herein) and/or on a test strip (e.g., a lateral flow bed/path used in a device described herein), pre-loaded with the plurality of binding agents propelled by a pulling force, such as capillary action. The device or strip is configured such that the liquid sample will come into contact with the plurality of binding agents prior to contacting the plurality of the capture agents in the capture zone. Suitable conditions may be applied to ensure complex formation between the target analyte and the binding agent and/or the capture agent. For example, in the first route (200), this first step can be carried out at room temperature, and/or optionally with slight heating provided sufficient time is allowed for the first complex and/or unbound target analytes and binding agents to interact with the plurality of capture agents so that the formation of the sandwich complex can be as complete as possible.

In the second route (300), the liquid sample is brought into contact with a plurality of capture agents disposed on a solid support in a lateral flow device or a test strip under conditions that permit formation of at least one complex between one target analyte and one capture agent prior to the liquid sample contacting the plurality of binding agents to form the sandwich complex. In practice, the liquid sample can flow through the lateral flow device first, followed by a separate subsequent flow of a buffer containing the plurality of binding agents.

According to one aspect, the sequential lateral flow device of this disclosure includes a housing unit having an inner surface that defines a cavity in the housing unit.

Figure 3:
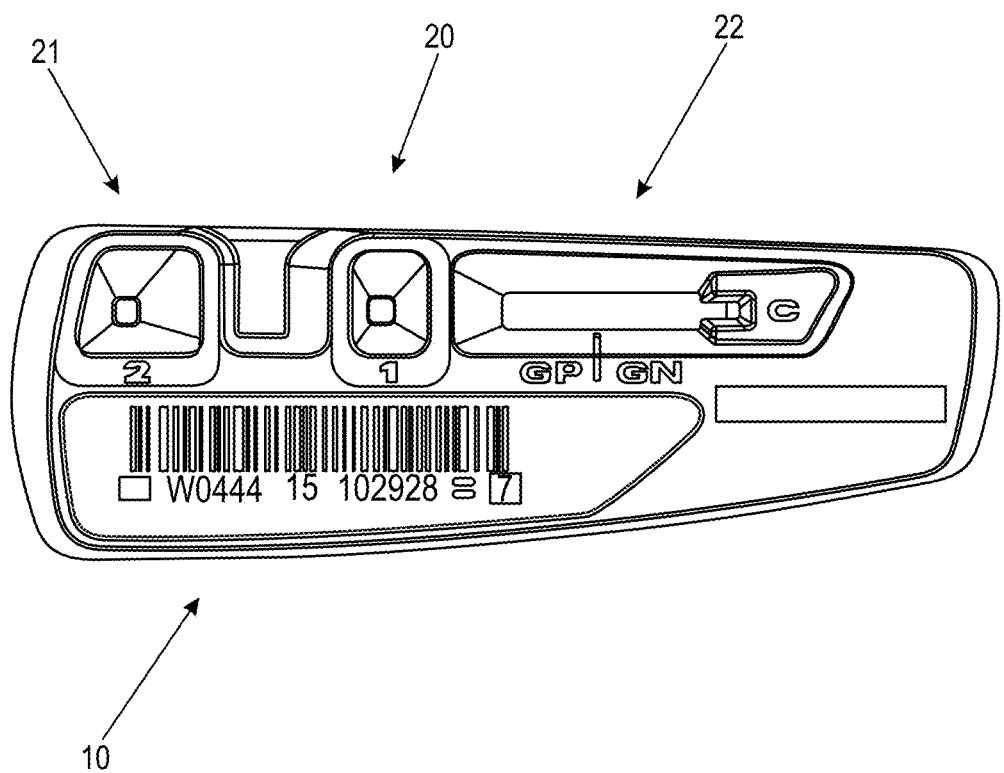
FIG. 3 shows a schematic illustration of the top view of a sequential lateral flow device according to some implementations.
Figure 4:
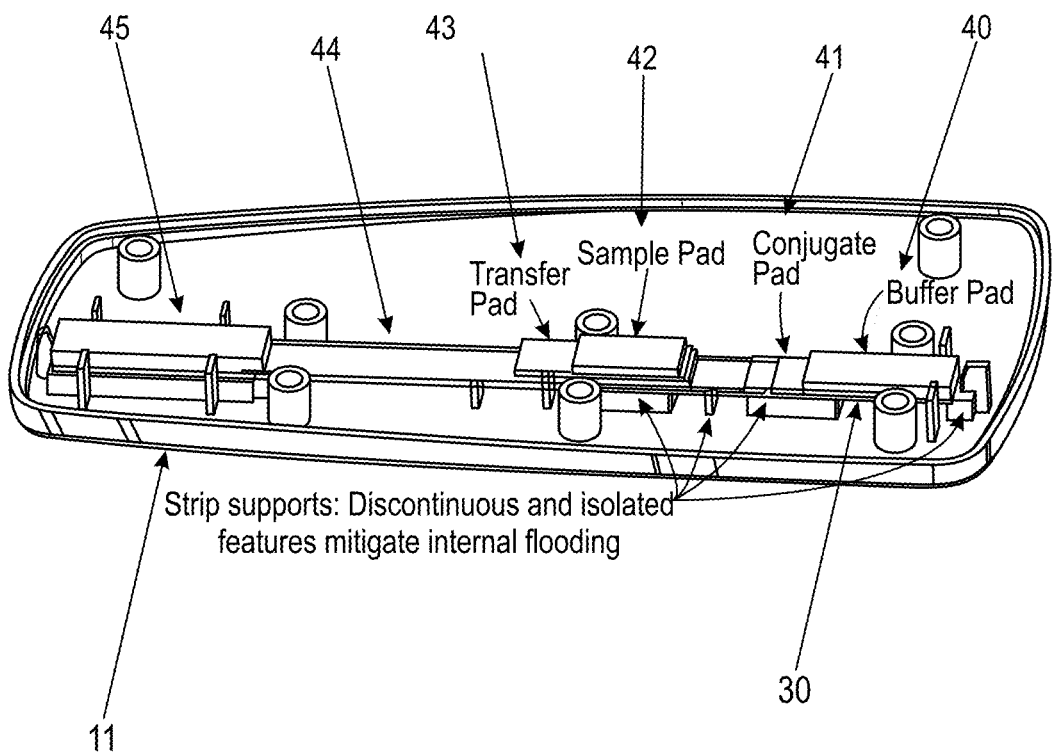
FIG. 4 shows a schematic illustration of a capillary flow bed residing inside the cavity of a housing unit according to some implementations.

FIGS. 3 and 4 show the top and inside views, respectively, of a sequential lateral flow device according to some implementations. As shown in FIG. 3, the housing unit may include an upper portion (10) that can fit together with a lower portion (11) (FIG. 4) to form the cavity. The upper portion of the housing unit may include a first inlet (20) (a portion of which is depicted in red and labeled with a "1" and a red outline in FIG. 3), a second inlet (21) (a portion of which is depicted in white and labeled with a "2" in FIG. 3), and a reading window (22). A liquid sample may be introduced through the first inlet (20) into the device, while a reagent buffer may be introduced through the second inlet (21) into the device.

FIG. 4 shows a capillary flow bed (30) residing inside the cavity of the housing unit, according to some implementations. In some implementations, the capillary flow bed has a proximal region and a distal region. In some implementations, the capillary flow bed is secured on the lower portion of the housing unit (11), which has limited contact points with the capillary flow bed (e.g., through discontinuous and isolated supports under the capillary flow bed), as shown in FIG. 4.

In some implementations, the housing unit may further include features such as datum and alignment tabs inside to keep the capillary flow bed properly aligned and secured inside the housing unit, e.g., on the lower portion of the housing unit. In some implementations, the housing unit may further include features, such as ribs, discontinuous supports, and/or pinch points inside, to control the flow of liquids passing through the capillary flow bed, such as in a sequential manner. In one aspect, the capillary flow bed is configured to transport liquids (e.g., the sample and the reagent buffer) from the proximal region to a distal region of the capillary flow bed through capillary action. Further features of the capillary flow bed are depicted herein, using like numerals as shown in FIG. 4, according to some implementations.

Figure 5A:
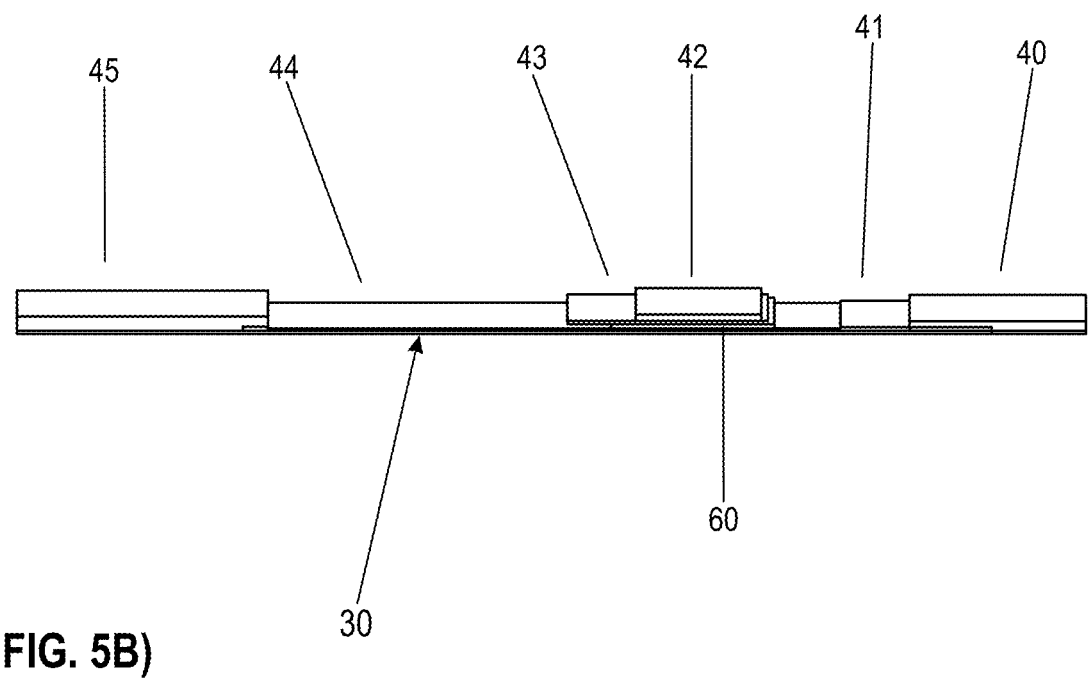
FIG. 5A shows a schematic illustration of a capillary flow bed, according to some implementations.
Figure 5B:
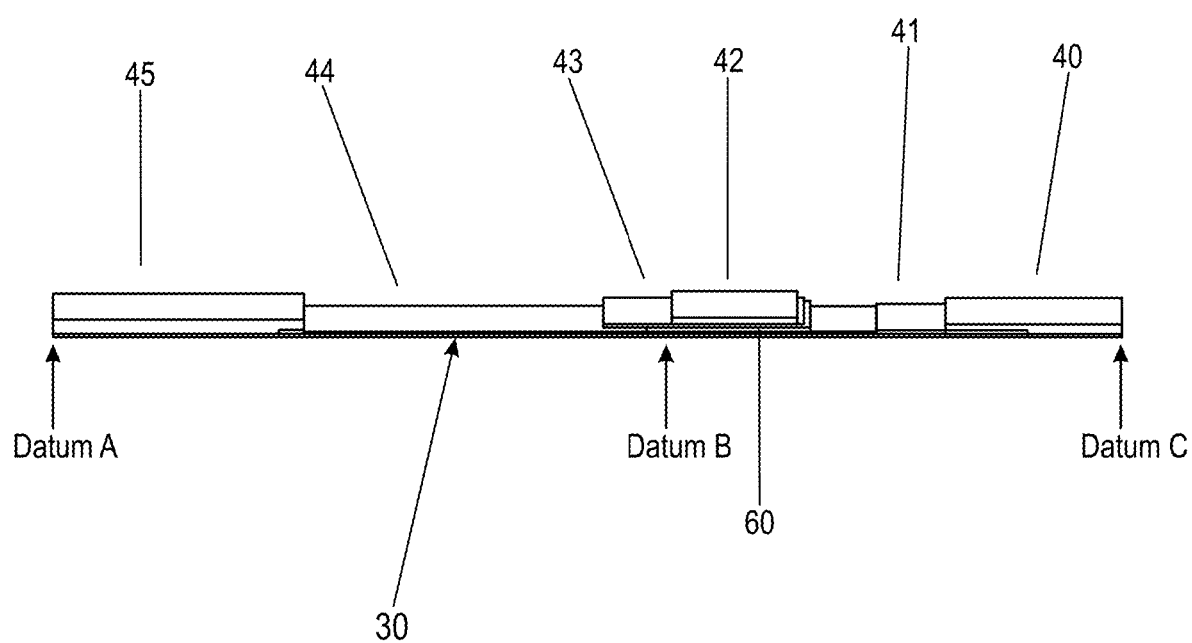
FIG. 5B shows a schematic illustration showing positioning of datum points in reference to the capillary flow bed, according to some implementations.

FIG. 5a shows the capillary flow bed and various components on the bed, according to some implementations. In some implementations, the capillary flow bed may include the following zones: a buffer receiving zone, a sample-receiving zone, and a capture zone. The buffer-receiving zone is disposed on the capillary flow bed and includes a buffer-receiving pad ($P_B$, 40) and a conjugate pad ($P_C$, 41). The conjugate pad includes (e.g., as attached thereto and/or associated therewith) a signaling agent (e.g., gold nanoparticles labeled with biotin-binding proteins) disposed therein for providing a detectable signal. The signaling agent may be releasably dried inside the conjugate pad (41). A reagent buffer may be introduced to the buffer-receiving pad through the second inlet (I2, 21) to mobilize the signaling agent retained in the conjugate pad to flow through the capillary bed toward the capture zone. The capture zone (C, 44) contains a plurality of capture agents (e.g., a plurality of capture agents of one or more than one type of capture agents), such as antibodies that specifically bind to a common antigen of a subset of the plurality of target analytes, immobilized on the capillary flow bed (e.g., in one or more than one groupings). In some implementations, the sequential lateral flow device may further include a reservoir pad (R, 45) disposed in the distal region of the capillary flow bed (30). The reservoir pad is adapted to draw the sample and the buffer carrying the mobilized signaling agent in the distal flow direction. In some implementations, the sample-receiving zone is disposed between the buffer-receiving zone and the capture zone. The sample-receiving zone includes a sample-receiving pad (Ps, 42) and a transfer pad (Pt, 43). According to some implementations, the sample-receiving zone also includes an impermeable backing (60). FIG. 5b shows the positions of datum points in reference to the capillary flow bed.

In some implementations, the device of the present disclosure comprises a capillary flow bed, such as those shown in FIGS. 5a and 5b. FIG. 5a shows the capillary flow bed with various components on the bed, according to some implementations. In certain such implementations, a sample-receiving zone (comprising a sample-receiving pad (42) and a transfer pad (43)), a buffer-receiving zone (a buffer-receiving pad (40) and a conjugate pad (41)), and a reservoir pad (45) are disposed on the capillary flow bed (30).

In some implementations, the capillary flow bed (30), and/or the sample-receiving pad (42), and/or the transfer pad (43), and/or the buffer-receiving pad (40), and/or the conjugate pad (41) may be made of a bibulous material, such as a nitrocellulose membrane. Bibulous material of the present disclosure is a porous material having pores, capable of transporting liquids through the material in response to capillary forces. The bibulous material comprises a series of fibers drawn together in parallel to form an open wick. The space between the fibers forms channels to draw liquids through capillary actions.

Generally, bibulous materials are hydrophilic in nature. Suitable bibulous materials include but are not limited to hydrophilic inorganic powders, such as silica gel, alumina, diatomaceous earth and the like, sponge materials, glass fibers, argillaceous substances, cloth, hydrophilic natural polymeric materials, particularly cellulosic material, like cellulosic beads, and especially fiber-containing papers such as filter paper and/or chromatographic paper, synthetic and/or modified naturally occurring polymers, such as nitrocellulose, cellulose acetate, polyvinyl chloride, polyacrylamide, polyethylene, glass fiber, polyacrylates, polyurethanes, crosslinked dextran, agarose, and other such crosslinked and non-crosslinked water-insoluble hydrophilic polymers. Suitable bibulous material of the present disclosure can be functionalized on the surface, for example, forming covalent bonds with antibodies and/or receptors.

In some implementations, the bibulous material can be in a form of pad, sheet, and/or compressed fibers. In some implementations, the bibulous material is nitrocellulose, such as nitrocellulose having a pore size from about 0.4 microns to about 15 microns.

In some implementations, the capillary flow bed is disposed on a solid support, such as a substantially impermeable support, including a water-insoluble, non-porous, flexible plastic strip, e.g., a polyester strip. In general, the solid support is of the same or slightly different dimension as the capillary flow bed. Suitable materials for the solid support include, but are not limited to, polyethylene, polypropylene, polystyrene, polymethacrylate, nylon, glass, ceramics, metals, polyurethane, neoprene, latex, silicone rubber, polyester, poly(ethylene terephthalate), poly(vinyl butyrate) and the like.

In some implementations, the capillary flow bed may include at least one capture zone (44), as shown in FIGS. 5a and 5b. A capture zone includes one or more than one capture agents immobilized on the capillary flow bed via chemical and/or physical means.

In some implementations, when the liquid sample is added to the sample-receiving pad (42), the sample flows to the transfer pad (43) under capillary forces and mixes with the plurality of binding agents to form a first complex between at least some of the binding agents and some of the target analytes. The sample carrying the first complex continues to flow via the capillary flow bed and through the capture zone. The plurality of capture agents then binds to the target analytes and forms a sandwich complex between the capture agents, target analytes, and the binding agents. Subsequently, as the buffer carrying the signaling agent flows through the capture zone, the signaling agent will bind to a binding agent of the sandwich complex through the conjugation pair and form a detection complex between the signaling agent, the binding agent, the analyte, and the capture agent. In some implementations, the first complex contacts the plurality of capture agents to form the sandwich complex such that the liquid sample contacts the plurality of capture agents only after formation of the first complex. The retained signaling agent thereby provides a detectable signal, indicating the presence of one or more than one of the plurality of target analytes in the sample. As such, the flow of liquids is tightly controlled in a sequential fashion, and the devices of this disclosure are designed in such a way to ensure the sequential and stepwise flow of liquids passing through the capillary bed.

In some aspects, various features of the capillary flow bed described herein may be incorporated to ensure sequential flow of fluids across the capillary flow bed (30) through the immobilized capture agents in the capture zone (44) and to minimize mixing of fluids at their interfaces. The sensitivity of the devices of this disclosure may result from a combination of the factors discussed herein, in particular, the sequential flow of the fluids and minimized mixing of liquids. In this disclosure, the liquids are referring to (1) a liquid sample mixed with a plurality of binding agents (e.g., antibodies, such as polyclonal antibodies); or (2) a buffer carrying signaling agents (e.g., streptavidin labeled gold nanoparticles).

In some implementations, the capillary flow bed may include a control zone, where the signalizing agent is being captured and retained even in the absence of the analyte as a means to indicate proper functioning of the device and/or to confirm the validity of the method performed. In some implementations, the control zone includes an immobilized member of the conjugation pair (e.g., biotin), which is able to bind to the signaling agent (e.g., streptavidin-labeled gold nanoparticles). In some implementations, the control zone may be disposed after the capture zone on the capillary flow in the distal region but before the reservoir pad.

In some implementations, as shown in FIGS. 5a and 5b, the capillary flow bed includes two fluid addition zones, namely, a sample-receiving zone and a buffer-receiving zone. In some implementations, the sample-receiving zone includes a sample-receiving pad (42) and a transfer pad (43). In some implementations, the buffer-receiving zone includes a buffer-receiving pad (40) and a conjugate pad (41).

As shown in FIGS. 5a and 5b, the sample-receiving zone is disposed in the middle of the capillary flow bed (e.g., in the middle lower third of the capillary bed) between the buffer-receiving zone and the capture zone (45), according to some implementations.

Figure 6:
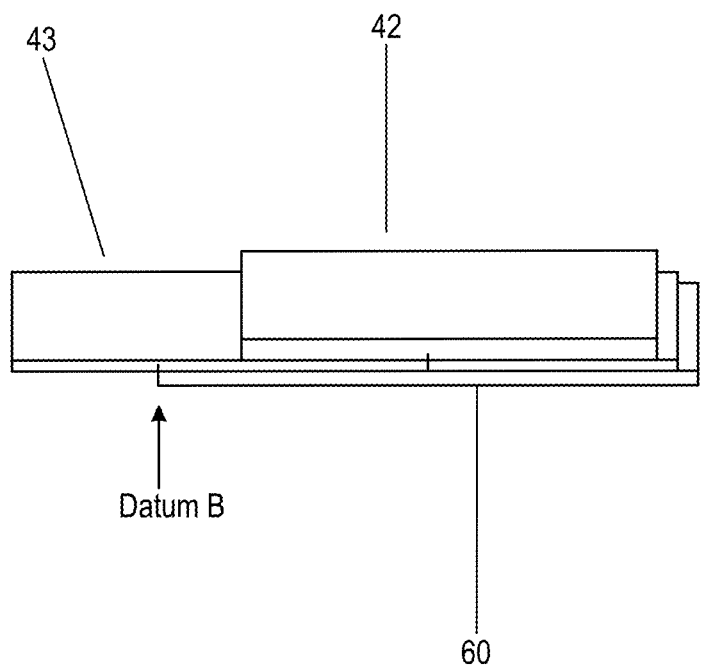
FIG. 6 shows a schematic illustration of the configuration of the sample-receiving zone, according to some implementations.

FIG. 6 shows an illustration of the sample-receiving zone, including a sample-receiving pad ($P_S$, 42) and a transfer pad ($P_T$, 43), according to some implementations. The sample-receiving zone of FIG. 6 may be used in any of the devices and/or methods disclosed herein. As shown in FIG. 6, a substantially impermeable backing (60) is disposed between the sample-receiving zone and the capillary flow bed and extending at least partially underneath the sample-receiving pad and the transfer pad. In some implementations, when the sample is introduced through the first inlet ($I_1$, 20) to the sample-receiving pad, the impermeable backing (60) inhibits contact between the sample and the capillary flow bed in the sample-receiving zone, thereby reducing backflow of the sample in a proximal direction. In some implementations, the plurality of binding agents, such as antibodies (e.g., biotin-labeled polyclonal antibodies) may be disposed inside the transfer pad. In some implementations, the binding agents may be dried inside the transfer pad and can bind to a common antigen of at least a subset of target analytes. In some implementations, the binding agents are contained within the sample-receiving pad.

In some implementations, the sequential lateral flow device is configured, and the method of use performed, such that the liquid sample flows along the capillary flow bed (30) into the capture zone (45) before the mobilized signaling agent flows into the capture zone (45). In some implementations, when in operation, the reading window (22) of the sequential lateral flow device is positioned over the capture zone (44) for observing a detectable signal produced by an interaction of the binding agent and the signaling agent in the presence of the target analytes.

The construction of the sample-receiving zone has been optimized to control and minimize the backward flow of the sample mixed with the binding agent (such as antibodies, e.g., biotinylated antibodies). In some implementations, the transfer pad (43) includes dried binding agents (e.g., antibodies) that will be reconstituted and mobilized upon addition of the sample to the sample-receiving pad through a first inlet (20). In some implementations, in order to minimize and control the backward flow of the sample and/or the first complex between the sample and the binding agent, the sample pad rests on a plastic backing (60) that is substantially impermeable and acts as barrier between most of the transfer pad and the capillary flow bed underneath (the capillary flow bed comprises a nitrocellulose pad). The only contact the transfer pad has with the capillary flow bed is via the forward lip of the transfer pad. It is only through this contact that any fluid will flow from the transfer pad onto the capillary flow bed.

Figure 7:
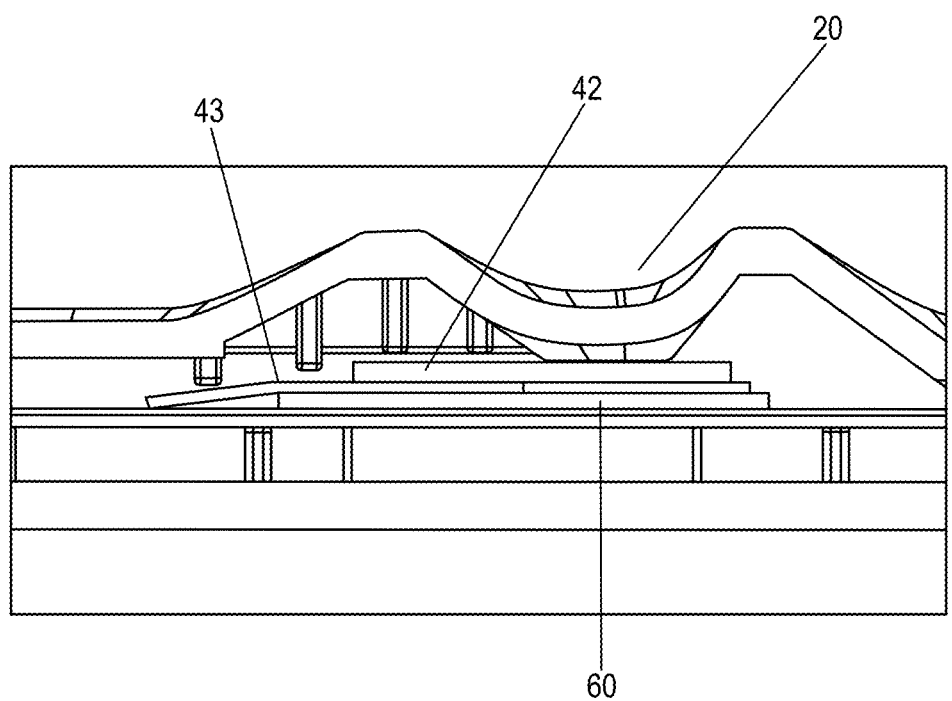
FIG. 7 shows a schematic illustration of the side view of the sample-receiving zone, according to some implementations.

FIG. 7 shows a schematic illustration of the side view of the sample-receiving zone inside the housing unit, according to some implementations. As shown in FIG. 7, the transfer pad may be bent at the forward tip section to come into contact with the capillary flow bed due to the impermeable backing (60) underneath, according to some implementations.

In some implementations, upon addition of the sample, the fluid will flow from the sample-receiving pad through the transfer pad and onto the capillary flow bed. This fluid will then flow forward toward the capture zone(s) and backwards toward the conjugate pad.

In some implementations, the buffer-receiving zone comprises a buffer-receiving pad (40) and a conjugate pad (41), as shown in FIGS. 4a and 4b. The buffer-receiving pad and the conjugate pad each comprise a bibulous material of the same or different kinds. Suitable buffer solutions to be used in this disclosure include but are not limited to a acetate buffer, buffered saline, citrate buffer, barbital buffer, phosphate buffer, or buffer prepared with tris(hydroxyl-methyl) aminomethane (TRIS), N-(2-acetamido)iminodiacetic acid (ADA), piperazine-1,4-bis(2-ethanesulfonic acid) (PIPES), N-(2-acetamido)-2-aminoethanesulfonic acid (ACES), N,N-bis(2-hydroxyethyl)-2-aminoethanesulfonic acid (BES), 3-morpholinopropanesulfonic acid (MOPS), N-tris(hydroxymethyl)methyl-2-aminoethanesulfonic acid (TES), 2,4-(2-hydroxyethyl)-1-piperazinyl ethanesulfonic acid (HEPES), 3,4-(2-hydroxyethyl)-1-piperazinyl propanesulfonic acid (EPPS), N-tris(hydroxymethyl)methylglycine (Tricine), N,N-bis(2-hydroxyethyl)glycine (Bicine), N-cyclohexyl-2-aminoethanesulfonic acid (CHES), N-cyclohexyl-3-aminopropanesulfonic acid (CAPS), and/or buffer containing one or more than one buffer salts selected from $K_2HPO_4$, $KH_2PO_4$, $Na_2HPO_4$, $NaH_2PO_4$, $NaHCO_3$, $NaBO_4$, $(NH_4)_2CO_3$.

After the liquid sample is added through the first inlet (20), the reagent buffer (such as a chase buffer, e.g., a phosphate buffer) may be introduced into the device through the second inlet (21) and onto the buffer-receiving pad (40) at the distal upstream end of the capillary flow bed. To avoid the situation where the binding agent (e.g., biotinylated antibodies) encounters and conjugates with the signaling agent (e.g., streptavidin-conjugated gold nanoparticles) beyond an insignificant amount at their fluid interface and to prevent sample fluid backflow to the conjugate pad, the buffer may be added as soon as the sample fluid front flows past the viewing window over the capture zone. The timing of adding the buffer ensures that there is a forward fluid counter-flow to the sample mixture flowing backwards. As a result, these two fluids will meet in a very small volume dictated by the pore size of the nitrocellulose pad of the capillary flow bed. Hence, very little mixing occurs between these two fluids.

The forward flow of the sample will reach the reservoir pad (45), which acts as a sump to draw fluid to itself. As long as this forward flow is imposed by the reservoir pad, there is very little mixing between the two fluids at their interface and their sequential flow is maintained. In some implementations, in roughly five to seven minutes, the sample fluid flow is complete and the flow front of the liquid containing the signaling agents should begin to appear in the reading window.

In some implementations, the device of this disclosure includes a reservoir pad (45). In some implementations, the reservoir pad is disposed in the distal region of the capillary flow bed, e.g., at the end of the distal region of the capillary flow bed. In some implementations, the reservoir pad also contains a bibulous material (e.g., a nitrocellulose pad), which serves as a liquid sink and has a liquid-absorbing capacity exceeding the sum capacity of the capillary flow bed, sample-receiving zone, and buffer-receiving zone combined. In this way, there is generated a continuous capillary force across the capillary flow bed from the proximal region to the distal region during the process of conducting the method. This continuous capillary force is important to keep the flow in one direction and lower the risk of backflow and/or fluids mixing.

In some aspects, there are many considerations for designing the housing unit, including manufacturability of the device, tolerances of the components, component sizes (e.g., component assembly and placement), functionality of the assay, (e.g., variability of how the assay is run due to user-related factors), and overall aesthetics. In some implementations, the device components may be secured in the housing unit so that various components of the device are properly aligned to inlets (or the liquid reagent wells) and the reading window. For example, as shown in FIGS. 2 and 3, the capture zone is presented in the reading window and the housing unit does not hinder testing and/or alter test results using the method disclosed herein. Various device components include, but are not limited to, a capillary flow bed, a buffer-receiving zone, a capture zone, a sample-receiving zone, and a reservoir pad to enable the method of detection. In other implementations, the housing unit may include features to facilitate the control and sequential flow of liquids (e.g., samples and the reagent buffer).

In some implementations, the dimensions of the housing are dictated in part by the requirement that the device can optionally be read by an off-the-shelf lateral flow assay (LFA) reader. Such LFA reader, e.g., Qiagen ESEQuant LR3, may dictate the device housing to be a certain size, for example, a size of less than about 110 mm long, about 50 mm wide and about 12.5 mm high. In addition to considerations of a LFA reader, the architecture of the capillary flow bed with various components of the device also influences the overall housing dimensions. In some implementations, the length of the capillary flow bed should be at least about 80 mm, at least about 90 mm, at least about 100 mm, or at least about 110 mm in order to facilitate the sequential flow of liquids and to accommodate liquid volume along with all the other components of the device. In some implementations, the length of the capillary flow bed may be in the range from about 50 mm to about 200 mm, from about 55 mm to about 180 mm, from about 60 mm to about 160 mm, from about 75 mm to about 140 mm, or from about 80 mm to about 100 mm. In some implementations, the capillary flow bed has a length of about 85 mm. However, the housing may be any suitable shape and/or size, including sizes that are not compatible with automated assay readers.

FIGS. 3 and 4 show the top and inside views of the housing unit, according to some implementations. In some implementations, the housing unit includes an upper portion (10) coupled to a lower portion (11). In certain such implementations, the upper portion of the housing unit includes a reading window (22). In some implementations, the upper portion of the housing unit further includes a first inlet (20), such as a first inlet for introducing the sample into the sample-receiving pad (42). In some implementations, the upper portion of the housing unit further includes a second inlet (21), such as a second inlet for introducing a buffer into the buffer-receiving pad (40).

In some implementations, to clearly differentiate the control line from other capture zones so that users could correctly interpret test results, the reading window is designed and disposed so as to clearly identify and isolate the control line from other capture zones.

FIG. 3 shows that the reading window is narrowed at the distal end, such as at the location of the control line, according to some implementations. In certain such implementations, the reading window may be narrowed from about 5 mm to about 3 mm. The narrowing creates a physical and visual differentiation that intuitively alerts the user that the control line is differentiated from other capture lines. In some implementations, the read window has a slope on the side walls away from the strip surface to minimize casting of shadows that can make it more difficult to properly visualize positive results.

In some implementations, the reading window has a length of from about 10-50 mm, from about 20-40 mm, or about 20 mm, about 30 mm, about 40 mm, or about 50 mm. In certain such implementations, the reading window has a length of about 23 mm.

In some implementations, the width of the reading window is less than the width of the capillary flow bed. In certain such implementations, the width of the reading window is from about 2 mm to 10 mm, from about 4 mm to 8 mm, from about 5 mm to 6 mm, or about 3 mm, about 4 mm, about 5 mm, or about 6 mm. In some implementations, the width of the reading window is about 4.7 mm. In other implementations, the width of the reading window is about 2.6 mm.

FIG. 3 shows that the upper portion of the housing (10) has a flat area on the top surface for labeling, such as for putting on a bar-code sticker, according to some implementations. In some implementations, the upper portion of the housing unit includes markings on its top surface to identify where sample and reagents are to be added. In some implementations, the upper portion of the housing unit has concaved surfaces around the first inlet and second inlet to form liquid reservoirs, which facilitate the transfer of liquids with a disposable pipette and dropper bottle.

In some implementations, the housing unit is designed for ease of manufacturing. For example, the upper and lower edges of the housing unit may be made parallel for a short segment to support automated sorting and alignment of the upper portion and the lower portion. In addition, the upper portion of the housing unit is modified in such a way that a standard roller-closure could be utilized for assembling the devices.

Figure 8A:
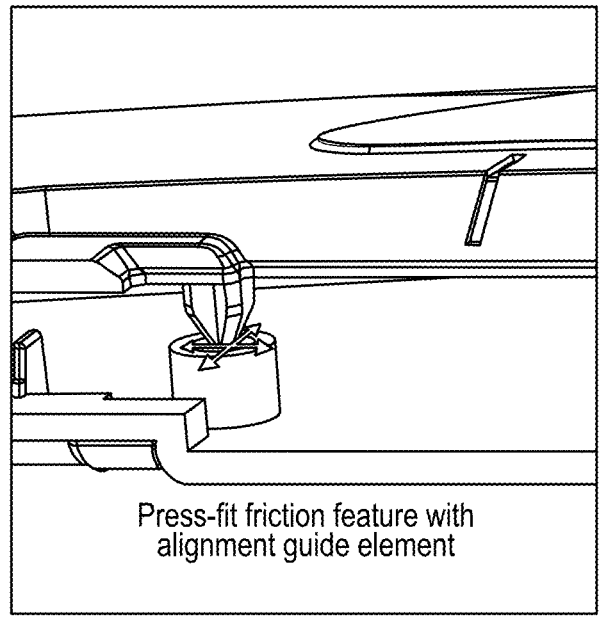
FIG. 8A shows a cut-away view of a housing alignment feature of friction-fit pins, according to some implementations.
Figure 8B:
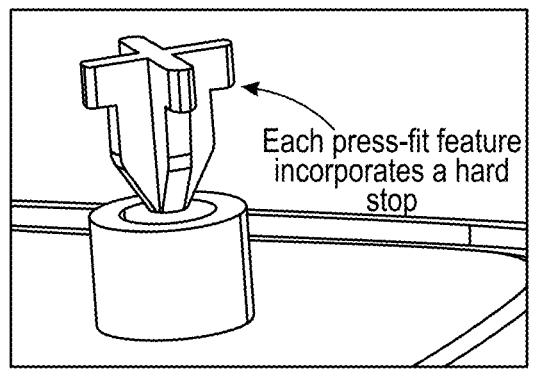
FIG. 8B shows each of the friction-fit pins having a hard stop figure that prevents over-closure of the device during assembly, according to some implementations.
Figure 8C:
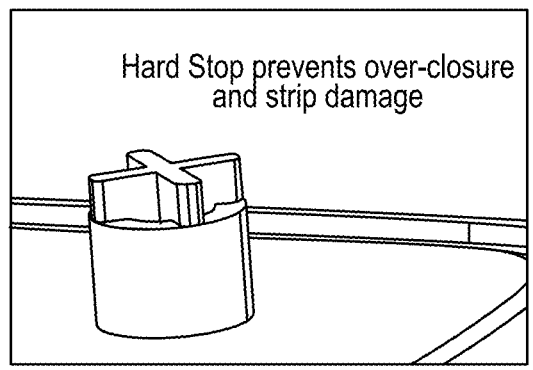
FIG. 8C shows that each of the friction-fit pins fully sits at the bottom of the cassette, according to some implementations.

In some implementations, the upper portion of the housing unit includes at least one friction-fit pin in its inner surface. FIGS. 8a-8c show the friction-fit pins with alignment guide elements, according to some implementations. In certain such implementations, the area under the friction-fit pins is substantially flattened to allow for uniform pressure against the pins critical for device closure. In some implementations, as shown in FIG. 8a, the friction-fit pins are cone-shaped so that the upper and lower portions of the housing unit can be aligned approximately and "honed in" during paring. In some implementations, the upper portion of the housing unit comprises one or more than one friction-fit pins, such as one, two, three, four, five, six, seven, eight, nine, or ten friction-fit pins.

FIGS. 8b and 8c show that, in addition to incorporating an alignment feature to the friction-fit pins, each of the friction-fit pins further has a hard stop feature that prevents over-closure of the device during assembly, which can potentially damage the capillary flow bed, according to some implementations.

The strategy for the design of the press-fit feature requires consideration of a number of other factors that are not readily apparent from a structural point of reference. One such consideration is the limitations of readily available toolmakers used to create the injection-molded housing unit. The toolmaker may have a limitation of not being able to reasonably rework the mold to create what is known as a "steel-safe" part. In some situations, the toolmaker, chosen for industry-leading rapid prototyping of injection-molded parts, can't rework the tool to tolerances less than 0.003 inches. Because of this limitation, the toolmaker cannot guarantee a snap and/or press-fit feature. To address this limitation, in some implementations, the friction fit feature incorporates a pin that would deform upon closure. In other implementations, the female component of the part can also deform to accommodate the pin. By designing the press-fit feature as deformable elements, the tolerance for acceptable interference fit is increased to about 0.005 inches and within tolerances of the conventional vendor's toolmaking capabilities.

Figure 9A:
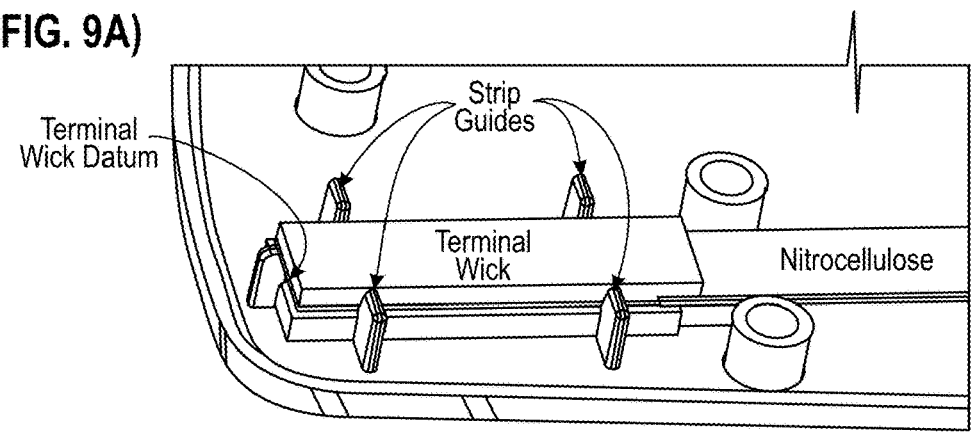
FIG. 9A shows a schematic illustration of guides for the capillary flow bed and the reservoir pad (terminal wick) datum, according to some implementations.
Figure 9B:
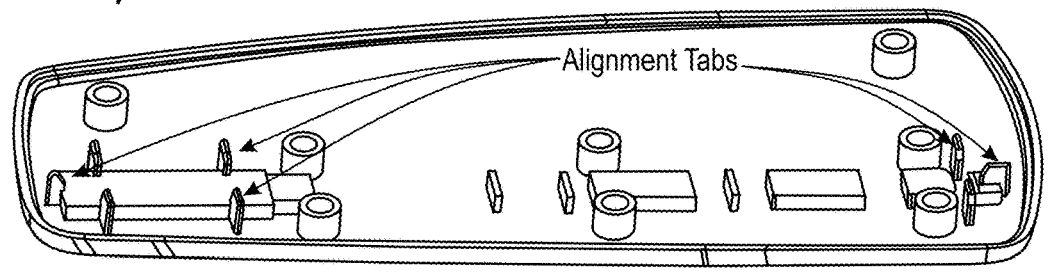
FIG. 9B shows a schematic illustration of alignment tabs to maintain the position of the capillary flow bed relative to housing features, according to some implementations.
Figure 9C:
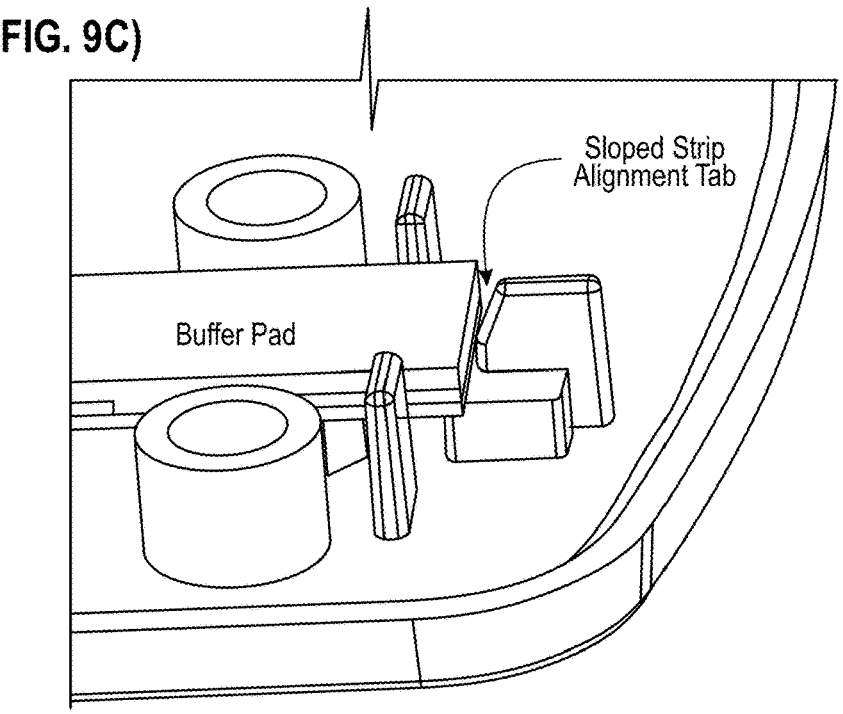
FIG. 9C shows a schematic illustration showing that alignment tabs slope away from the capillary flow bed, aiding assembly and preventing flooding, according to some implementations.

One aspect of the housing design is the need to properly secure the capillary flow bed and each component on top of it into the desired position. FIGS. 9a-9c show alignment tabs and datum and their positioning in the inner surface of the housing unit, according to some implementations. FIG. 9a shows that the capillary flow bed and the housing unit may reference a common datum located at the distal region of the capillary flow bed, such as located at the reservoir pad (or terminal wick) end of the capillary flow bed, according to some implementations. In certain such implementations, it is from this common datum that the capillary flow bed and the housing unit tolerances are derived. In some implementations, the datum for the housing unit is a tab that the distal region of the capillary flow bed is butted.

FIG. 9b shows alignment tabs in the inner surface of the housing unit to maintain the position of the capillary flow bed, according to some implementations. In certain such implementations, besides the terminal-wick-datum-point-tab in the housing unit, the devices of this disclosure further include a series of alignment tabs (such as two or more alignment tabs, e.g., two, four, six, or eight alignment tabs) that align the capillary flow bed to the appropriate features of the housing unit. These alignment tabs keep the capillary flow bed centered with the first and second inlet (i.e., sample and buffer wells) as well as the critical pinch points that are at the interface between the housing unit and the capillary flow bed.

FIG. 9c shows alignment tabs slope away from the capillary flow bed to aid assembly and prevent flooding, according to some implementations. In certain such implementations, the capillary flow bed and the components thereon may be properly placed either manually and/or by automation. To make this task easier, the alignment tabs are sloped in such a way to help guide the capillary flow bed into proper position. In some instances, the housing may provide a potential point of wetting and unintentionally flood the interior and/or cavity of the housing unit. In some implementations, to avoid situations like unintentional flooding, the alignment tabs may slope aggressively away from the surface of the capillary flow bed so that the liquid reagents are contained within the confines of the pads and features of the housing unit.

In some aspects, the methods and devices of this disclosure are designed to detect multiple target analytes, such as bacterial antigens from a vast variety of bacterial species and strains. In some implementations, the methods and devices of this disclosure may use a large number of complex antibody mixtures. In some implementations, multiple capture zones of antibodies may be immobilized on the capillary flow bed (e.g., a nitrocellulose pad) in the devices of this disclosure. The wide variation of antigen targets means that in order to facilitate detection, the detector antibodies must be equally diverse and present in a sufficient quantity to label enough antigens to produce a detectable signal. It is determined that better performance of using the devices of this disclosure is achieved by sequentially flowing the sample, including labeled antibodies, across the capture zones and then followed by the detector component (such as a signaling agent, e.g., streptavidin-conjugated colloidal gold particles). The specific need to sequentially flow the sample and reagents (e.g., a buffer solution) in a controlled, reproducible and robust manner through the device presents unique challenges for the device design.

A number of features may be incorporated in the sequential lateral flow device to ensure containment and controlled release of liquids, according to some implementations. For example, the housing unit of the devices of the present disclosure may be involved in the handling of liquids within the devices during use. In some implementations, to facilitate a sequential delivery of liquids (e.g., the sample and the reagent buffer), crude and variable amounts of liquids must be contained and later be released from a reservoir and/or area of containment. In some implementations, in practice, the user will add a sample through the first inlet (e.g., the sample well). In some implementations, the sample will wet out the sample-receiving pad and then wet out the transfer pad containing binding agents, such as antibodies.

In some aspects, the sample-receiving pad and the transfer pad do not have the capacity to completely contain the liquid sample. However, the liquid sample must still be controlled and/or held back to prevent flooding out of the flow path on the capillary bed because the flooding will result in the sample liquid flowing over instead of through the pores of the nitrocellulose pad of the capillary flow bed that contains the capture agents (e.g., the capture antibodies). Furthermore, if the liquid sample and/or buffer is not adequately contained, the sample and buffer could leave the desired flow path and flood out the interior and/or cavity of the housing unit. In either circumstance, the detection will be compromised. To support a sequential delivery of each liquid independently, it is challenging to retain and release the liquid in the device and to control the flow of any liquid into the flow path (e.g., nitrocellulose flow path) at a desired time point. The same challenge applies to the buffer and buffer-receiving pad, as well as the conjugate pad.

Figure 10:
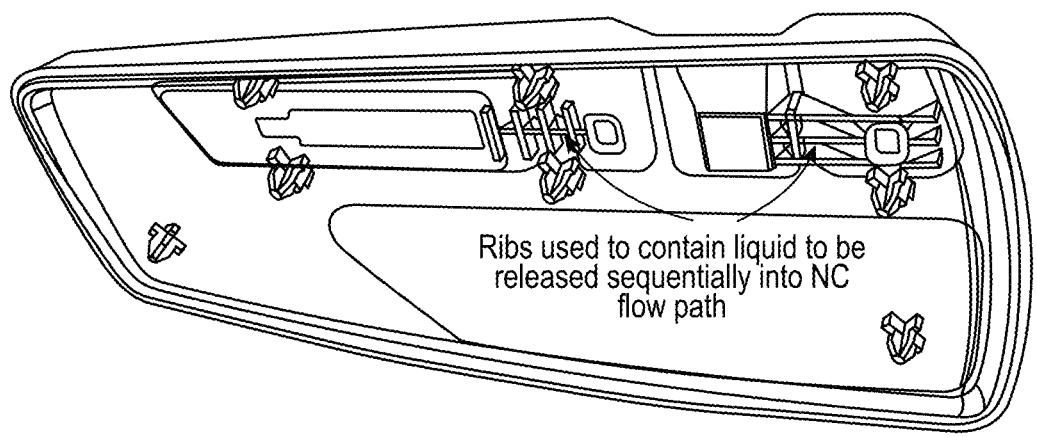
FIG. 10 shows a schematic illustration of liquid containment ribs that serve as a liquid reservoir inside the upper portion of the housing unit, according to some implementations.

In some implementations, the housing unit may interact with the pads and facilitate containment and release of the liquid sample and buffer to the capillary flow bed (the nitrocellulose pad) in a sequential manner FIG. 10 shows a schematic illustration of the inner surface of the housing unit (e.g., the upper portion) having a series of ribs, according to some implementations. In certain such implementations, a series of ribs is incorporated into the housing unit, such as in the inner surface of the upper portion of the housing unit, to facilitate the sequential flow of liquid sample and the buffer. In some implementations, the ribs are approximately perpendicular and/or approximately parallel to the capillary flow bed (e.g., the nitrocellulose flow path).

FIG. 10 shows that the ribs may be disposed on the inner surface of the upper portion of the housing unit, such as over the sample-receiving pad and/or over the buffer-receiving pad, according to some implementations.

In some implementations, the housing unit may comprise a plastic material as the surface energy and/or wettability of plastic material can contribute to the liquid containment and/or release. For example, plastic material may have a lesser ability to hold onto liquids than the bibulous material of the capillary flow bed. As such, plastic material may be particularly suitable for the housing unit due to the need to facilitate readily releasing liquids into the capillary flow bed (e.g., nitrocellulose) to the point of capillary saturation. As liquids move through the capillary flow bed to the reservoir pad (e.g., the terminal wick), fluid contained in the housing unit is sequentially released to flow through the sample-receiving pad, to the capillary flow bed, and toward the reservoir pad (e.g., the terminal wick). In some implementations, the ribs can hold the liquids in place until the capillary flow bed (e.g., nitrocellulose) becomes incrementally less saturated. At this point, more liquid is then transferred to the transfer pad from the sample-receiving pad that remains saturated by the liquids held by the wetted housing features. The size and spacing of the ribs determine how much excess liquid may be contained in the device.

Interestingly, according to some implementations, once the liquid sample and/or the buffer is depleted to the point of becoming less saturated, the excess liquid from the inlet (e.g., the sample and/or buffer well) of the device becomes available to the capillary flow bed. In certain such implementations, this process continues as the bibulous material (e.g., nitrocellulose pad) of the capillary flow bed becomes incrementally less saturated and it, hence, becomes a source of capillarity and draws liquid from the liquid-saturated conjugate pad. As analogously described for the sample-receiving pad and the transfer pad, the over-saturated buffer-receiving pad, in turn, saturates the conjugate pad. The buffer-receiving pad is maintained in an oversaturated state by drawing a buffer that is held in place by the ribs on the inner surface of the upper portion of the housing unit just under the second inlet (i.e., the buffer well), according to some implementations.

In some implementations, to run an assay with the disclosed devices, the liquid sample and buffer are added to the device in excess of any of the pads' capacity to fully absorb the volume required. In some implementations, excess liquid is introduced to the device because the pads must "give up" the liquids to the nitrocellulose of the capillary flow bed. This oversaturated state inevitably leads to a propensity of the liquids to flood within the device and/or not be sufficiently contained to prevent method failure. To prevent potential flooding in the housing unit, a number of structural features may be incorporated into the device, such as in the housing unit, according to some implementations.

The capillary flow bed and the reservoir pad comprise the primary liquid flow pathway in the device. Feeding into this primary flow pathway is the liquid sample and the reagent buffer originating from the first inlet and the second inlet, respectively. Once these liquids are introduced to the device, the liquids will saturate the sample-receiving pad and the buffer-receiving pad, respectively, and begin to pool on any wettable surface. This situation produces a dynamic in which part of the liquids will flow over the surface of the capillary flow bed and have no contact with the capture zone within the pores (e.g., nitrocellulous pores) of the capillary flow bed.

Figure 11:
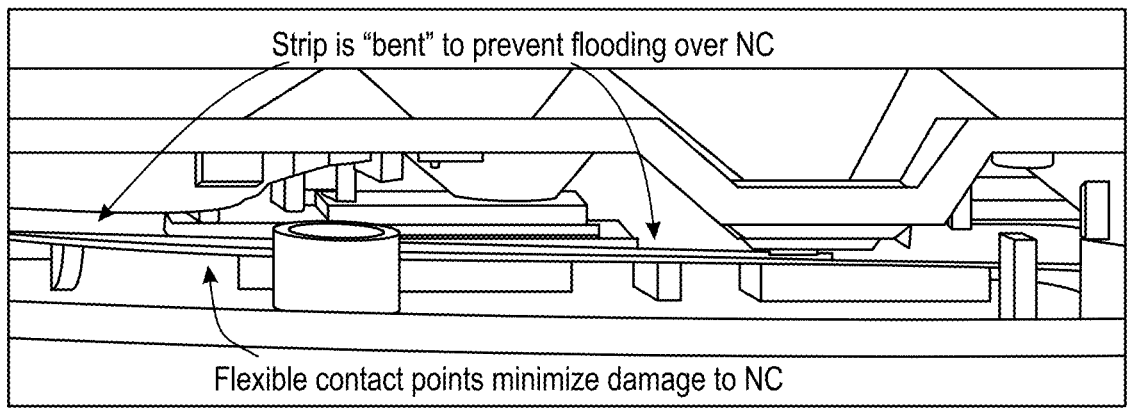
FIG. 11 shows a photograph showing the bend of the capillary flow bed inside the cavity of the housing unit, according to some implementations.
Figure 12A:
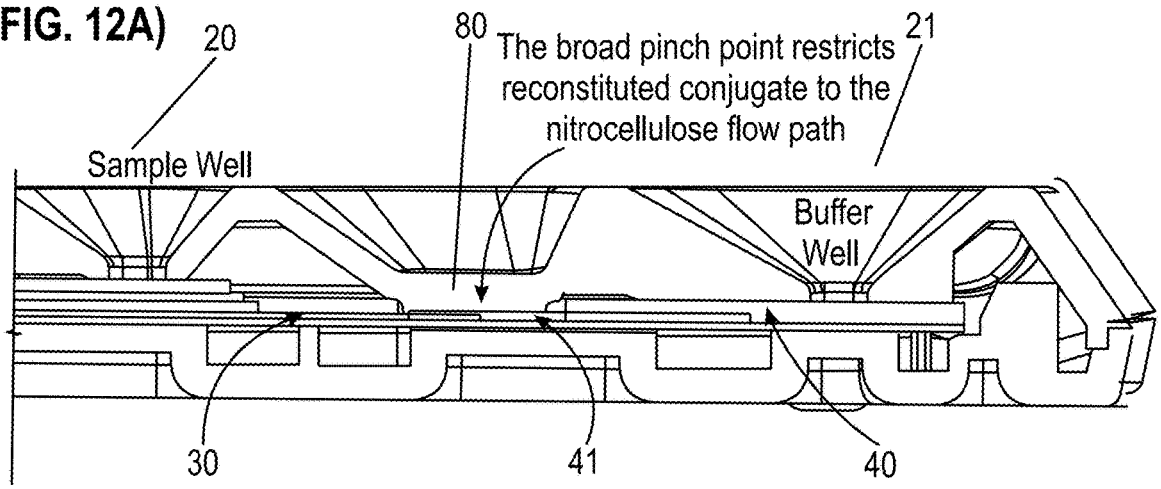
FIG. 12A shows a schematic illustration of broad pinch contact points inside the housing unit to compress the conjugate pad to direct the liquid flow into the capillary flow path, according to some implementations.
Figure 12B:
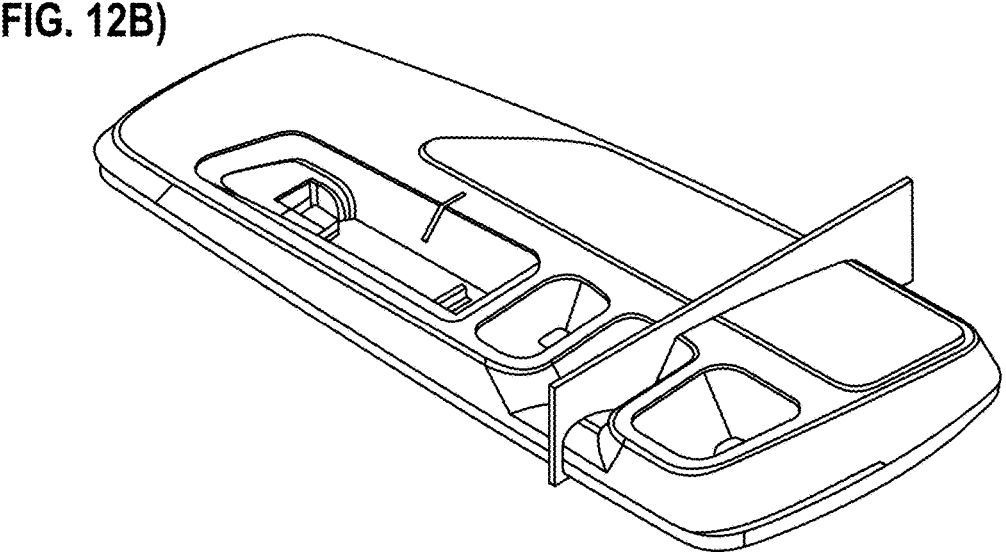
FIG. 12B shows a schematic illustration showing positioning of the cross-section view of the broad pinch point in FIG. 12C.
Figure 12C:
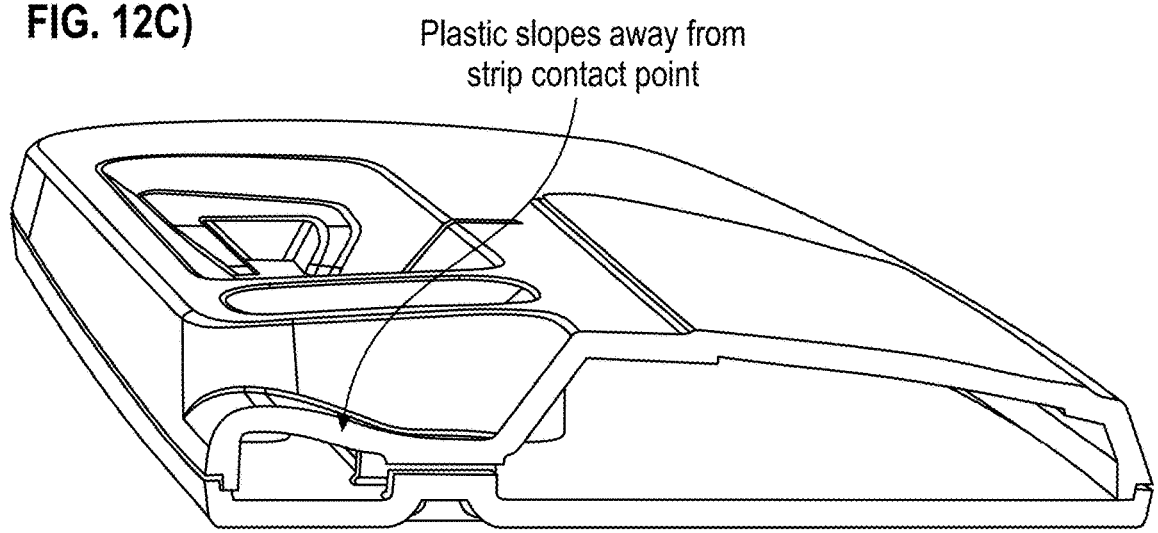
FIG. 12C shows the cross-section view of the broad pinch point, in which the housing plastic slopes away from the contact point with the capillary flow bed, according to some implementations.
Figure 12D:
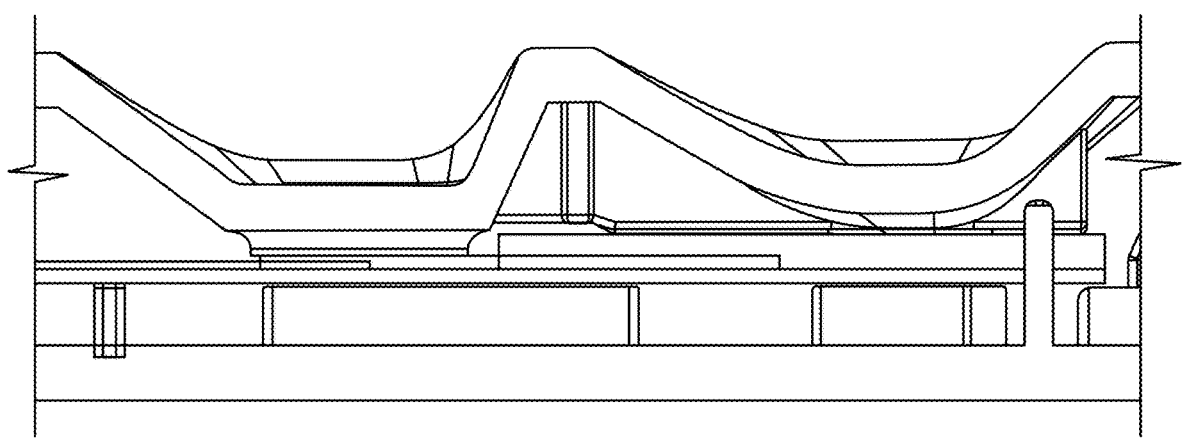
FIG. 12D shows a schematic illustration of the cross-section view of the broad pinch point in reference to the sample-receiving zone according to some implementations.

FIG. 11 shows that, to prevent overflow, the capillary flow bed may be bent so that the liquids enter into the pore structures (e.g., nitrocellulose pores) of the capillary flow bed, according to some implementations. Basically, the bending in the capillary flow bed forces the liquids to enter into the nitrocellulose pore structures of the capillary flow bed though capillary action.

FIG. 11 also shows bending the capillary flow bed to prevent liquid from flowing over the surface of the bed, according to some implementations. In certain such implementations, the capillary flow bed is bent so that the contact point of the transfer pad is anywhere from about 0.02 mm to about 1 mm lower than one or more adjacent flow bed supports. This (roughly) amounts to about 0.05 degrees to about 10 degrees of a bending angle. The bend encourages capillarity flow and mitigating flow over the capillary bed surface, so that excess reagent added to the wells and some liquid on the capillary flow bed will pool in locations adjacent to the liquid reservoirs, thereby reducing localized flooding, which will diminish the sequential delivery of fluids from the reservoirs.

FIGS. 12a-12d show the broad pinch points incorporated on the underside of the housing unit, according to some implementations. In certain such implementations, a broad area of contact is incorporated in the housing unit, such as in the upper portion of the housing unit, to compress the conjugate pad and thereby direct the reconstituted conjugate to flow into the nitrocellulose pores of the capillary bed. It was determined that this broad area contact, acting as a broad pinch-point, may facilitate a more compact and discrete flow of conjugate through the device.

Theoretically, every point where the capillary flow bed contacts the housing unit may become a location that can create a capillary action. This occurs because liquids are able to wet the surfaces of plastic materials and, once wet, the contact point becomes a point for internal flooding. In some implementations, features of the housing unit that contacts the capillary flow bed may be incorporated to prevent capillarity from creating an undesired and/or otherwise uncontrolled pathway for the liquids to follow.

FIG. 4 shows an open view of the sequential lateral flow device, having the capillary flow bed secured in the lower portion of the housing unit, according to some implementations. In some implementations, the housing unit, such as the lower portion of the housing unit, may also incorporate features that represent limited contact points with the capillary flow bed that are isolated from other portions of the capillary flow bed. In certain such implementations, the lower portion of the housing unit may include discrete and discontinuous supporting blocks, as shown in FIG. 4. In certain such implementations, the supporting blocks are disposed under the capillary flow bed at positions corresponding to the sample-receiving pad. In other implementations, the supporting blocks are disposed under the capillary flow bed at positions corresponding to the buffer-receiving pad, e.g., aligned to the second inlet. In some implementations, the supporting blocks are disposed under the capillary flow bed at positions corresponding to the reservoir pad.

In some implementations, the supporting blocks under the first inlet are only long enough to provide support for the capillary pad, the first inlet, and associated pinch points. In some implementations, the supporting blocks under the second inlet are only long enough to provide support for the capillary pad, the second inlet, and associated pinch points.

Figure 13:
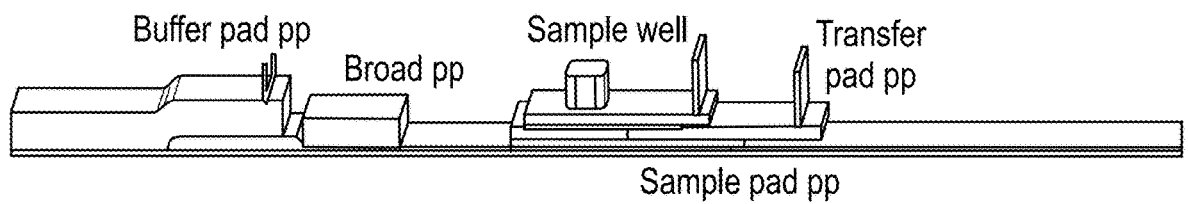
FIG. 13 shows a schematic illustration of the positions of pinch points relative to the capillary flow bed, according to some implementations.

FIG. 13 shows positions of the pinch points in the housing unit in reference to the capillary flow bed, according to some implementations. In certain such implementations, the housing unit may include one or more than one pinch point in the housing unit, such as in the inner surface of the housing unit. The purpose of pinch points is to assure that the different components on the capillary flow bed (such as sample-receiving pad, buffer-receiving pad, reservoir, conjugate pad, and transfer pad) are in contact with adjacent components so that a reliable and reproducible flow path is established in the device. In some implementations, a pinch point presses the buffer-receiving pad into the conjugate pad thereby creating a flow path for the buffer to flow to the conjugate pad. In some implementations, a pinch point presses the conjugate pad into the capillary flow bed (nitrocellulose) thereby creating a flow path for the sample and the analyte-binding agent to flow to the capillary flow bed. In some implementations, a pinch point presses the sample-receiving pad into the transfer pad to create a flow path for the sample to flow from the sample-receiving pad to the transfer pad. In some implementations, a pinch point presses the transfer pad into the capillary flow bed to create a flow path for the sample to flow from the transfer pad to the capillary flow bed. In some implementations, the pinch points exert sufficient pressure to facilitate a reproducible liquid flow path in materials that are compressible, such as the capillary flow bed. For example, the pinch point can exert enough forces to assure a continuous flow pathway, but not restrictive and/or damaging to the individual components of the device, according to some implementations.

The sequential lateral flow devices suitable for use in the methods of the present disclosure may be selected from any of the implementations of the sequential lateral flow devices and/or kits described above and/or below.

Reagents suitable to use in the methods, devices, and/or kits of the present disclosure include the following, but are not limited to the following.

In some implementations, the methods and devices of the present disclosure include a signaling agent. The signaling agent is capable of producing a detectable signal, such as a visually detectable signal, a chemically detectable signal, an electromagnetically detectable signal, and/or a signal detectable by an instrument to report the presence of analytes in a tested sample. Various signaling agents suitable for use in the methods and/or devices of this disclosure include agents that produce signals through chemical and/or physical means. For example, the signaling agent may be a particle, such as a colored particle, a latex particle, a metallic particle (e.g., gold, silver, platinum nanoparticles, and/or colloidal metallic particles), a fluorescent particle, a magnetic particle, a chemiluminescent particle, a non-metallic colloidal particle, and/or a luminescent particle. Other suitable signaling agents include, but are not limited to, liposomes, plastic and/or polymeric particles, stained microorganisms, cells, enzymatic substrates and/or enzymes (e.g., catalytic enzymes), specific-binding substances, and/or any vesicles containing visible substances and the like.

In some implementations, when the signaling agent is a particle, the particle size can be in a range from about 30 nm to about 120 nm in diameter, or from about 40 nm to about 100 nm in diameter, or from about 50 nm to about 90 nm in diameter, or from about 60 nm to about 80 nm in diameter. In some implementations, the particle size is about 40 nm, about 60 nm, or about 80 nm in diameter. In some implementations, the particle size is about 40 nm in diameter.

In some implementations, the signaling agent provides a detectable signal, such as a detectable signal in the capture zone of the device where the binding agent bound analytes are captured by the capture agent.

In some implementations, the signaling agent (e.g., signaling particle) is dried within the conjugation pad.

In some implementations, the signaling agent is attached and/or labeled with a first or second member of a conjugation pair. In certain such implementations, the signaling agent is associated and/or labeled with a first or second member of a conjugation pair and the binding agent is attached and/or labeled with a second or first member of a conjugation pair.

In some implementations, the signaling agent comprises gold nanoparticles (such as about 40 nm, about 60 nm, or about 80 nm gold nanoparticles) labeled with a first member of a conjugation pair, for example avidin, streptavidin, and/or other biotin binding proteins and/or antibodies, while the binding agent may be labeled to a second member of the conjugation pair, such as biotin and/or any avidin binding moieties.

In some implementations, the methods and devices of the present disclosure may include a plurality of binding agents. In certain such implementations, each of the plurality of binding agents may be labeled with a first or second member of a conjugate pair, such as biotin and/or any avidin binding moieties and/or molecules. In some implementations, the binding agent may be present in the transfer pad, such as in a dry form in the transfer pad. In some implementations, the binding agent may be contained in the sample-receiving pad.

In some implementations, the plurality of binding agents of this disclosure are antibodies and/or a functional fragment thereof, e.g., antibodies that specifically bind a common antigen of at least a subset of a plurality of Gram-negative bacteria and/or antibodies that specifically bind a common antigen of at least a subset of Gram-positive bacteria. In some implementations, the binding agents are polyclonal antibodies, such as one or more than one type of a multivalent polyclonal antibody. In other implementations, the binding agents are monoclonal antibodies. In some implementations, the plurality of binding agents comprises one or more than one type of antibodies or two or more than two types of antibodies, wherein each antibody specifically binds a common antigen of a subset of bacteria in a liquid sample.

In some implementations, the polyclonal antibody binds lipoteichoic acid (LTA). In some implementations, the polyclonal antibody binds a bacterial lipopolysaccharide structure (LPS). In some implementations, at least one type of the plurality of binding agents specifically bind a Gram-positive bacterial antigen and at least one type of the binding agents specifically bind a Gram-negative bacterial antigen. In some implementations, the plurality of binding agents are capable of binding one or more than one (e.g., two or more, three or more, four or more) genera of bacteria.

In some implementations, the antibody is selected from a polyclonal antibody, a monoclonal antibody and a combination of polyclonal and monoclonal antibodies. In some implementations, the antibody is polyclonal and binds a common antigen of a plurality of bacteria. In some implementations, the antibody is polyclonal and binds a common antigen of a plurality of Gram-positive bacteria and/or a plurality of Gram-negative bacteria, and/or both. In some implementations, at least one antibody is a monoclonal antibody and at least one antibody is a polyclonal antibody. In some implementations, at least one antibody specifically binds a common antigen of Gram-positive bacteria and at least one antibody specifically binds a common antigen of Gram-negative bacteria. In some implementations, the antibody is capable of binding one or more than one (e.g., two or more, three or more, four or more) genera of bacteria.

In some implementations, such binding agents comprise antibodies which bind under physiological conditions to an antigen-containing epitope of a lipopolysaccharide (LPS) structure of a Gram-negative bacteria and/or a lipoteichoic acid (LTA) structure of a Gram-positive bacteria.

Antibodies useful in the methods and devices of the disclosure include, but are not limited to, a monoclonal antibody, a polyclonal antibody, a single-chain antibody, a synthetic antibody, a recombinant antibody, a chimeric antibody, and/or any antigen-binding fragment of the above, including, but not limited to, F(ab), F(ab'), F(ab')$_2$, scFv fragments and recombinant fragments. The antibodies may be from non-species, for example, a chicken antibody, and/or from a mammalian species, including but not limited to rabbits, rodents (including mice, rats and guinea pigs), goats, pigs, sheep, camels and humans. The antibodies also may be humanized and/or chimeric antibodies.

Those skilled in the art are enabled to make any such antibody derivatives using standard art-recognized techniques. For example, Jones et al. (Nature 321: 522-525 (1986)) discloses replacing the CDRs of a human antibody with those from a mouse antibody. Marx (Science 229: 455-456 (1985)) discusses chimeric antibodies having mouse variable regions and human constant regions. Rodwell (Nature 342: 99-100 (1989)) discusses lower molecular weight recognition elements derived from antibody CDR information. Clackson (Br. J. Rheumatol. 3052: 36-39 (1991)) discusses genetically engineered monoclonal antibodies, including Fv fragment derivatives, single-chain antibodies, fusion proteins, chimeric antibodies and humanized rodent antibodies. Reichman et al. (Nature 332: 323-327 (1988)) discloses a human antibody on which rat hypervariable regions have been grafted. Verhoeyen et al. (Science 239: 1534-1536 (1988)) teaches grafting of a mouse antigen binding site onto a human antibody.

Preferably, the antibodies of the present disclosure are polyclonal antibodies and/or monoclonal antibodies. Generation of monoclonal and polyclonal antibodies is well within the knowledge of one of ordinary skill in the art of biology (see, e.g., Ausubel et al., Current Protocols in Molecular Biology, John Wiley & Sons, New York, N.Y., 1994). A number of procedures are useful in producing antibodies to the desired unique target antigens. Traditional immunization and harvesting techniques will result in the creation of polyclonal antibodies directed against the common determinants of the target bacterial species including determinants such as LPS and LTA. Additionally, cellular hybridization techniques can be utilized to produce immortal hybridoma cell lines that generate specific monoclonal antibodies to the target species.

Antibodies having potential utility for broadly detecting Gram-positive bacteria include those described in Fisher et al., PCT Publication No. WO98/57994; Jackson, D. E. et al., Infection and Immunity 43: 800 (1984); Hamada, S. et al, Microbiol. Immunol. 28: 1009 (1984); Aasjord, P. et al., Acta Path. Microbiol. Immunol. Scand. Sect. C, 93: 245 (1985); McDaniel, L. S. et al., Microbial Pathogenesis 3: 249 (1987); Tadler, M. B. et al., Journal of Clinical Laboratory Analysis 3: 21 (1989); and Stuertz, K et al., Journal of Clinical Microbiology 36: 2346 (1998).

Antibodies having potential utility for broadly detecting Gram-negative bacteria include those described in Nelles, M. J. et al, Infect. Immun 46: 677 (1984); Teng, N. N. H. et al, Proc. Natl. Acad. Sci. USA 82: 1790 (1985); Dunn, D. L. et al., Surgery 98: 283 (1985); De Jongh-Leuvenink, J. et al, Eur. J. Clin. Microbiol. 5: 148 (1986); Bogard, W. C. et al., Infect. Immun 55: 899 (1987); Pollack, M. et al., Bacterial Endotoxins: Pathophysiological Effects, Clinical Significance, and Pharmacological Control. pp. 327-338 Alan R. Liss, Inc. (1988); Priest, B. P. et al., Surgery 106: 147 (1989); Tyler, J. W. et al., Journal of Immunological Methods 129: 221 (1990); Siegel, S. A. et al., Infect. Immun 61: 512 (1993); Shelburne, C. E. et al., J. Periodont. Res. 28: 1 (1993); Di Pardova, F. E. et al., Infect. Immun 61: 3863 (1993); and De Kievit, T. R. and Lam, J. S. J. Bacteriol. 176: 7129 (1994).

The antibody or antibodies used can be selected using classical techniques. Antibody specificity, binding extent and kinetics can be characterized by empirically testing each antibody in an empirical format. Micro-titer screening formats are well documented in the literature to aid in characterizing specific antibody response in any given immunoassay format. Likewise, the activities of detectably labeled antibodies can be characterized by executing a variety of chemical conjugation techniques and screening the resulting product for the optimal performance parameters. The capture antibody and detectably labeled antibody can be screened against the clinical isolates of bacteria from retained platelet or red cell samples to emulate final assay performance as close to final product embodiment as possible. This experimentation leads to the selection and optimization of antibody reagents for application in the various assay formats described below.

Monoclonal antibodies with specificity towards cross-genus targets on the bacterial cell surfaces may be utilized in methods and of the present disclosure. In some implementations, blends of monoclonal antibodies may be utilized. Polyclonal antibodies, including polyclonal antisera and/or polyclonal mixtures made by blending monoclonal and/or polyclonal antibodies with broad specificity across the different Gram-negative and Gram-positive species are useful in the methods and devices of the present disclosure.

In some implementations, the antibodies disclosed herein can be utilized as described and/or modified as necessary to produce a useful agent.

In some implementations, the methods and devices of this disclosure may include a plurality of capture agents. The plurality of capture agents can be immobilized on a solid support, such as immobilized on a capillary flow bed covalently through a chemical bond, and/or the plurality of capture agents can be immobilized through absorption, according to some implementations.

In some implementations, the plurality of capture agents are antibodies and/or a functional fragment thereof, such as any of the antibodies described in this disclosure. In some implementations, the capture agents include the same type of antibodies as the plurality of binding agents. In other implementations, the capture agents include different types of antibodies from the plurality of binding agents. In some implementations, the plurality of capture antibodies are immobilized in groups in one or more than one location on a solid support (e.g., on a capillary flow bed), such as in one or more than one location on the solid support (e.g., one or more than one location within the capture zone of a capillary flow bed). In some implementations, the capture agents are immobilized in one or more than one locations within the capture zone on a capillary flow bed. In some implementations, the plurality of capture agents comprise one or more than one capture agent grouping on the solid support, the groupings spatially separated from each other and each grouping includes an antibody that specifically binds to a different common antigen of at least a subset of the target analytes.

In one aspect, this disclosure provides a kit for detecting and/or screening a plurality of target analytes (e.g., bacteria, viruses, and/or fungi) in a liquid sample. The kit may include any one of the devices of this disclosure, a dropper with fixed volume calibration to the capacity of the sample-receiving pad, a buffer solution and/or buffer salts for preparing a buffer solution, and one or more than one reagent for pre-treating the liquid sample. The kit may further include instructions providing procedural steps for using the device and/or control reagents as positive and/or negative controls. In some implementations, the kit may be used to perform any method of the present disclosure. In some implementations, detecting and/or screening a plurality of target analytes comprises detecting the presence of a plurality of target analytes, such as target analytes of a clinically relevant amount.

Variations and modifications will occur to those of skill in the art after reviewing this disclosure. The disclosed features may be implemented, in any combination and sub-combination (including multiple combinations and sub-combinations), with one or more other features described herein. The various features described and/or illustrated above, including any components thereof, may be combined and/or integrated in other systems. Moreover, certain features may be omitted and/or not implemented.

It is important to note that the constructions and arrangements of features and/or the components thereof as shown in the various exemplary implementations are illustrative only. Although only a few implementations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the teachings and advantages of the subject matter disclosed. For example, elements shown as integrally formed may be constructed of multiple parts and/or elements, the position of elements may be reversed and/or otherwise varied, and the nature and/or number of discrete elements and/or positions may be altered and/or varied. The order and/or sequence of any process and/or method steps may be varied and/or re-sequenced according to alternative implementations. Other substitutions, modifications, changes and omissions may also be made in the design, operating conditions and arrangement of the various exemplary implementations without departing from the scope of the present disclosure.

While various implementations have been described and illustrated herein, those of ordinary skill in the art will readily envision a variety of other mechanisms and/or structures for performing the function and/or obtaining the results and/or one or more of the advantages described herein, and each of such variations and/or modifications is deemed to be within the scope of the implementations described herein. More generally, those skilled in the art will readily appreciate that, unless otherwise noted, any parameters, dimensions, materials, and configurations described herein are meant to be exemplary and that the actual parameters, dimensions, materials, and/or configurations will depend upon the specific application and/or applications for which the teachings is/are used. Those skilled in the art will recognize, and/or be able to ascertain using no more than routine experimentation, many equivalents to the specific implementations described herein. It is, therefore, to be understood that the foregoing implementations are presented by way of example only and that, within the scope of the appended claims and equivalents thereto; implementations may be practiced otherwise than as specifically described and claimed. Implementations of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

In this disclosure, a sample can be any liquid sample that is suspected of containing bacteria, virus, and/or fungi. In some implementations, the sample is a biological fluid, including urine, sputum, spinal fluid, ascites, blood and blood products, e.g., blood and/or a blood product. In some implementations, the blood and/or blood product is selected from the group consisting of: whole blood, leukocytes, hematopoietic stem cells, platelets, red blood cells, plasma, bone marrow and serum.

In some implementations, this disclosure provide devices, kits, and methods for detecting a broader range of bacterial genera, species, and/or strains of bacteria in platelet storage samples. Platelets and/or thrombocytes are blood components that are responsible for coagulation and wound-healing. Platelets are transfused to supplement patients with low platelet counts, such as leukemia patients, cancer patients undergoing chemotherapy and/or radiation treatment, patients with auto-immune diseases, patients in surgery and/or who have traumatic injuries and/or infections. In general, it is difficult to preserve and/or store platelets for long term use as platelets have a short shelf life of 5 days and have to be stored at room temperature (chilled platelets are quickly scavenged by the liver). Thereby, they are susceptible to bacterial contamination during storage from the donor's skin flora. Transfusion of a contaminated platelet unit can cause sepsis in the patient resulting in morbidity and/or death; therefore, it is critical to detect bacteria contamination in platelet storage and prior to transfusion.

Current practice in determining safety of platelets for transfusion depends on sample storage bag 24-hour post-collection and using a culture growth method for bacteria detection. The culture based tests cannot eliminate false negatives due to insufficient sampling of ultra low CFUs at the early lag phase of bacterial growth. In addition, when used within hours of transfusion, the culture-based tests may still need a minimum number of hours for results.

In some implementations, the blood and/or a blood product such as platelets is from a donor for transfusion to a recipient. In some implementations, the sample is a dialysis sample, such as a dialysis sample selected from hemodialysis fluid and peritoneal dialysis fluid. In some implementations, the sample is a fluid in which a tissue such as a tissue from a donor for transplanting to a recipient has been stored. In certain such implementations, the tissue is selected from the group consisting of: blood cell cultures, stem cell cultures, skin and bone and cartilage graft materials. In some implementations, the sample is derived from lung, bronchoalvealor, peritoneal, and/or arthroscopic lavage. In other implementations, the sample is an environmental sample such as water and soil. In some implementations, the sample is food and/or a beverage. Those of skill in the art will recognize that, in cases where the sample source is in solid form, such as soil and/or solid foods, the sample may be a liquid extract of the solid form and/or liquid that has been in contact with the solid form. In some implementations, the sample is a biological sample, for example, urine, tears, sputum and/or cerebrospinal fluid.

In some implementations, the sample of this disclosure is pre-treated via a chemical and/or mechanical means. For example, in some implementations, an appropriate volume of the liquid sample is mixed with a pre-treatment reagent such that fragments of the cell wall structure are knocked off into the sample. This treatment results in the exposure of a binding site of the target analyte (e.g., exposure of antigen and/or antigenic component of bacteria). The suitable pre-treatment reagent may be a chemical, such as a surfactant, a chelator, and/or an enzyme to degrade macromolecular structures and expose the native antigenic structure. The treatment may also be by mechanical means, using mechanical fragmentation (such as sonication) and/or kinetic energy (such as boiling) to break down the cell wall into its sub-components, thereby exposing a binding site of a binding agent on an antigenic component. In other implementations, the sample is based-shocked and followed by neutralization by a neutralizing agent. For example, the sample is mixed with a base solution (e.g., NaOH solution), which acts as a lysing solution to break down the cell walls, then followed by neutralization with a neutralizing agent. Such sample pretreatment also serves to dissociate bacteria and bacterial fragments that may be bound to endogenous antibodies and binding factors from the donor.

In some implementations, the pre-treated sample is mixed with a plurality of binding agents. In certain such implementations, the plurality of binding agents comprise antibodies, e.g., a detector antibody, such as polyclonal antibodies or multivalent polyclonal antibodies. In some such implementations, the binding agents are in a solution containing the neutralizing agent.

In some implementations, the sample is treated prior to or concomitantly with contacting the sample with an antibody. In some implementations, the antibody can bind to a common antigen of at least a subset of the target analytes. For example, the antibody can bind bacterial lipoteichoic acid (LTA) or bacterial lipopolysaccharide structure (LPS). In some implementations, the antibody may be an antibody capable of binding more than one genus of bacteria, viruses, and/or fungi. For example, the treatment exposes a binding site on the Gram-negative bacterial antigen and/or on the Gram-positive bacterial antigen for the antibody. A binding site on a bacterial antigen may be exposed by, for example, cleaving an antigen from the cell wall and/or cell pad of the bacteria, thereby exposing the binding site; inducing the bacteria to secrete the antigen, thereby exposing the binding site; lysing the bacteria, thereby releasing an intracellular bacterial antigen and thus exposing the binding site on the antigen; and/or by inducing a conformational change on the bacterial antigen, thereby exposing the binding site. Such treatments include mechanical disruption of the bacterial cells in the sample by physical means, including, without limitation, sonication, boiling, and/or homogenization, using, for example, a Dounce homogenizer. The treatment may also be treatment of the sample by chemical means with a compound and/or composition, such as a detergent, a basic solution (for alkaline lysis), an acidic solution (for acidic lysis), EDTA, EGTA, a metal ion, an anion, a cation, a surfactant, a chelator, and/or an enzyme (e.g., lysostaphin, lysozyme, mutanolysin, labiase, achromopeptidase, trypsin, proteinase K, an autolysin, bacteriophage-encoded lytic enzymes, and combinations thereof). The treatment exposes a binding site for the antibody on the Gram-negative bacterial antigen and/or on the Gram-positive bacterial antigen. The treatment also dissociates bacteria or bacterial antigen bound to endogenous antibodies and binding factors.

It is anticipated that the various implementations discussed herein are combinable, and may indeed be combined with any particular implementation of the system, device, or method without departing from the scope of the invention.

Examples

1. Detecting Various Bacteria in Blood Samples Using the Sequential Lateral Flow Device in Comparison with Detection with a Non-Sequential Lateral Flow Device (Direct Assay).

TABLE 1

| Strain | Direct Assay LOD | Sequential Dipstick LOD | Improvement |
|---|---|---|---|
| Pseudomonas aeruginosa 10145 | 2.15e6 | 3.7Ee4 | ~2 logs |
| Staphylococcus epidermidis 147 | 1.15e5 | ≤1.2e4 | ≥1 log N |
| Staphylococcus aureus 25923 | 5.90e5 | 1.1e5 | ½ log |
| Bacillus cereus 7064 | 2.60e4 | 3.0e3 | 1 log |
| Streptococcus mitis 6249 | ND at 1e6 | 1.1e5 | >1 log |
| Streptococcus pneumoniae 6303 | ND at 1e6 | 1.2e4 | >2 logs |
| Streptococcus oralis 9811 | ND at 1e6 | 3.7e4 | ~2 logs |
| Clostridium perfringes 13124 | 3.40e5 | <1.2e4 | >1 log |

2. Use of a Sequential Lateral Flow Device of this Disclosure for Bacteria Detection.

The aim of this experiment was to compare the ability to detect bacterial antigen by performing an assay in a sequential and non-sequential delivery of sample and reagents through a test strip. The sample was prepared from 10-fold dilutions of *Pseudomonas aeruginosa* ATCC 27853. Detection of bacterial antigen was facilitated by scanning the signal generated from colloidal gold immobilized on the nitrocellulose through an immunological assay within striped bands of immobilized capture antibodies. Quantification of immobilized colloidal gold was facilitated by scanning with a Qiagen ESEQuant LR3 reader utilizing LFStudio software ver. 3.6.0 with the baseline set at 30 units. Quantification of the *Pseudomonas aeruginosa* ATCC 27853 bacteria was performed using a dilution plate count (DPC) method. This is the typical method used by microbiologists and is known to those skilled in the art.

Figure 14:
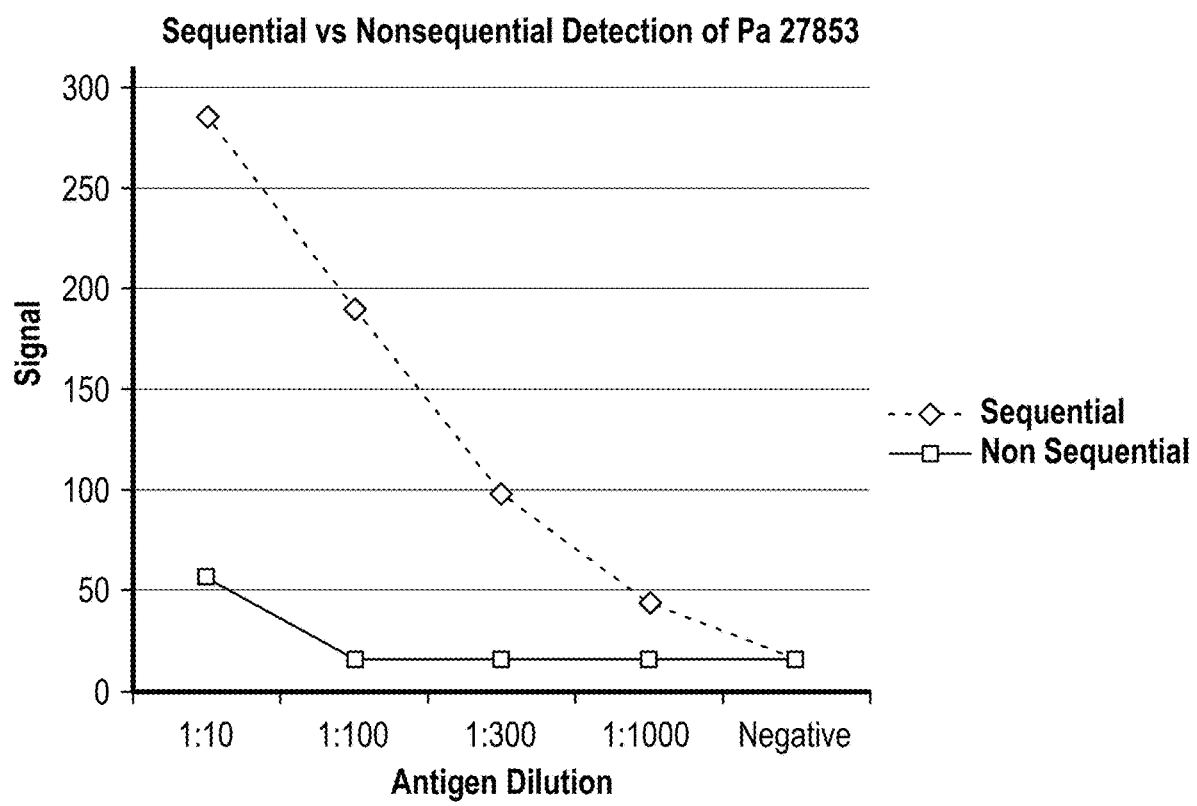
FIG. 14 shows a quantitative comparison of detection signals for detecting Pa 27853 at various dilutions using a non-sequential lateral flow device (direct method) vs. a sequential lateral flow device, according to some implementations.
Figure 15:
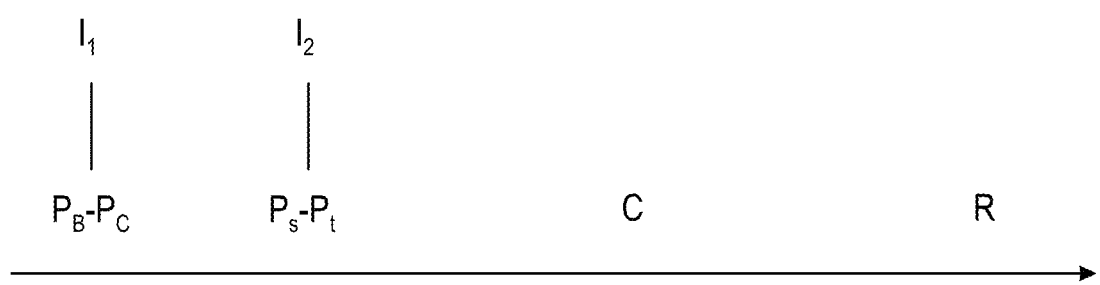
FIG. 15 shows an arrangement of the sample-receiving zone, the buffer-receiving zone, the capture zone, and the reservoir pad from the proximal region to the distal region on the capillary flow bed.

In this Dilution Plate Count method, 100 μL of platelet sample containing Pa 27853 was serially diluted by 10-fold with a fresh platelet sample. After a 36 hour incubation of time, the Colony Forming Units (CFU) were counted to determine the number of bacteria contained in the initial sample. These 10-fold diluted samples were then run in an assay utilizing either a sequential or non-sequential delivery of sample and reagents to the test strip. To make the direct comparison of sequential to non-sequential performance, all components including the prepared sample were identical. The results of this experiment are shown in FIG. 14.

Variations and modifications will occur to those of skill in the art after reviewing this disclosure. The disclosed features may be implemented, in any combination and sub-combination (including multiple dependent combinations and sub-combinations), with one or more other features described herein. The various features described and/or illustrated above, including any components thereof, may be combined and/or integrated in other systems. Examples of changes, substitutions, and alterations are ascertainable by one skilled in the art and could be made without departing from the scope of the information disclosed herein. Moreover, certain features may be omitted and/or not implemented. All references cited are hereby incorporated by reference herein in their entireties and made part of this application.

What is claimed is:

1. A lateral flow device for detecting a plurality of target analytes in a liquid sample, the device comprising:
   a housing unit comprising an inner surface that defines a cavity in the housing unit;
   a capillary flow bed residing in the cavity, wherein the capillary flow bed transports the liquid sample from a proximal region of the capillary flow bed to a distal region of the capillary flow bed;
   a buffer-receiving zone comprising a buffer-receiving pad ($P_B$) and a conjugate pad ($P_C$), the conjugate pad comprising a signaling agent for providing a detectable signal;
   a capture zone (C) comprising a plurality of immobilized capture agents;
   a sample-receiving zone disposed between the buffer-receiving zone and the capture zone, the sample-receiving zone comprising a sample-receiving pad ($P_S$), a transfer pad ($P_T$), and a substantially impermeable backing disposed between the sample-receiving zone and the capillary flow bed and extending at least partially underneath the sample-receiving pad and the transfer pad, the transfer pad comprising a plurality of binding agents that specifically bind to a plurality target analytes;
   a bibulous reservoir pad (R) disposed in the distal region of the capillary flow bed;

a first inlet ($I_1$) in said housing for introducing the liquid sample into the sample-receiving pad, wherein the impermeable backing inhibits contact between the liquid sample and the capillary flow bed in the sample-receiving zone, thereby reducing backflow of the sample in a proximal direction;

a second inlet ($I_2$) in said housing for introducing a buffer into the buffer-receiving pad, wherein the buffer mobilizes the signaling agent to obtain a mobilized signaling agent; and a reading window defined in the housing unit over the capture zone for observing a detectable signal produced by an interaction of the binding agent and the signaling agent in the presence of the target analyte;

wherein the bibulous reservoir pad draws the liquid sample and the mobilized signaling agent in the distal flow direction, and wherein the liquid sample flows along the capillary flow bed into the capture zone before the mobilized signaling agent flows into the capture zone.

2. The lateral flow device of claim 1, wherein the inner surface of the housing unit comprises a series of ribs which retain excess fluid, thereby inhibiting the excess fluid from overflowing the sample-receiving pad or the buffer-receiving pad.

3. The lateral flow device of claim 2, wherein the series of ribs are disposed over the sample-receiving pad on the upper inner surface of the housing unit.

4. The lateral flow device of claim 2, wherein the series of ribs are disposed over the buffer-receiving pad on the upper inner surface of the housing unit.

5. The lateral flow device of claim 1, wherein the inner surface of the housing unit comprises at least one pinch point pressing the buffer-receiving pad into the conjugate pad to create a flow path for the buffer to flow from the buffer-receiving pad to the conjugate-pad.

6. The lateral flow device of claim 1, wherein the inner surface of the housing unit comprises at least one pinch point pressing the sample-receiving pad into the transfer pad to create a flow path for the liquid sample to flow from the sample-receiving pad to the transfer-pad.

7. The lateral flow device of claim 1, wherein the inner surface of the housing unit comprises at least one pinch point pressing the transfer pad into a flow path bed to create a flow path for the liquid sample from the transfer-pad to the capillary flow bed.

8. The lateral flow device of claim 1, wherein the capillary flow bed is slightly bent to promote capillary action and minimize flooding.

9. The lateral flow device of claim 1, wherein the plurality of capture agents in the capture zone comprise one or more types of capture agents each adapted to a common antigen of at least a subset of target analytes in the liquid sample.

10. The lateral flow device of claim 1, wherein the plurality of the capture agents bind a Gram-positive and/or Gram-negative bacterial antigen.

11. The lateral flow device of claim 1, wherein the plurality of the capture agents comprise antibodies.

12. The lateral flow device of claim 1, wherein the plurality of capture agents comprise one or more capture agent groupings on the capillary flow bed, the groupings spatially separated from each other, each grouping comprising an antibody that binds to a different target or analyte.

13. The lateral flow device of claim 1, wherein the plurality of binding agents bind a Gram-positive and/or Gram-negative bacterial antigen.

14. The lateral flow device of claim 1, wherein the plurality of binding agents comprise antibodies.

15. The lateral flow device of claim 1, wherein each of the plurality of binding agents is labeled with a first member of a conjugate pair and the signaling agent is labeled with a second member of the conjugate pair.

16. The lateral flow device of claim 15, wherein the conjugate pair comprises biotin and a biotin-binding protein, and either the binding agent or the signaling agent is labeled with biotin.

17. The lateral flow device of claim 1, wherein the capillary flow bed comprises nitrocellulose.

18. The lateral flow device of claim 1, wherein the sample-receiving pad, the buffer-receiving pad, the bibulous reservoir pad, and the conjugate pad each comprises a bibulous material.

* * * * *